US008415321B2

(12) United States Patent
Schinazi et al.

(10) Patent No.: US 8,415,321 B2
(45) Date of Patent: Apr. 9, 2013

(54) **NUCLEOSIDE DERIVATIVES FOR TREATMENT OF *CALICIVIRIDAE* INFECTIONS, INCLUDING NOROVIRUS INFECTIONS**

(76) Inventors: Raymond F. Schinazi, Atlanta, GA (US); Richard Anthony Whitaker, Loganville, GA (US); Tamara Rosario McBrayer, Atlanta, GA (US); Steven J. Coats, McDonough, GA (US)

( * ) Notice: Subject to any disclaimer, the term of this patent is extended or adjusted under 35 U.S.C. 154(b) by 697 days.

(21) Appl. No.: 12/421,362

(22) Filed: Apr. 9, 2009

(65) Prior Publication Data

US 2009/0280084 A1    Nov. 12, 2009

Related U.S. Application Data

(60) Provisional application No. 61/045,064, filed on Apr. 15, 2008.

(51) Int. Cl.
*A61K 31/7068* (2006.01)
*C07H 19/067* (2006.01)

(52) U.S. Cl.
USPC .......................................... 514/49; 536/28.5

(58) Field of Classification Search ........................ None
See application file for complete search history.

(56) References Cited

U.S. PATENT DOCUMENTS

| 4,046,879 | A | 9/1977 | Swetly |
| 6,777,395 | B2 * | 8/2004 | Bhat et al. ........................ 514/43 |
| 6,828,105 | B2 * | 12/2004 | Stein et al. .................... 435/6.16 |
| 2006/0040890 | A1 | 2/2006 | Martin et al. |
| 2007/0298093 | A1 * | 12/2007 | Konur et al. .................. 424/450 |

FOREIGN PATENT DOCUMENTS

| WO | 03039450 A2 | 5/2003 |
| WO | 2004002999 A2 | 1/2004 |
| WO | 2006133497 A1 | 12/2006 |
| WO | 2007112348 A2 | 10/2007 |

OTHER PUBLICATIONS

Remington: THe Science and Practice of Pharmacy, 20*th* Edition, edited by Alfonso R. Gennaro, published 2000 by Lippincott Wiliams and Wilkins, pp. 704-712, 858-859, 1112-1114.*

Chang et al., "Interferons and Ribavirin Effectively Inhibit Norwalk Virus Replication in Replicon-Bearing Cells" Journal of Virology (2007) vol. 81, No. 22, p. 12111-12118.*
Merriam-Webster's Collegiate Dictionary, Tenth Edition, published 1998 by Merriam-Webster, incorporated, p. 924.*
Jiang et al., "Norwalk Virus Genome Cloning and Characterization" Science (1990) vol. 250 pp. 1580-1583.*
Fukushi et al., "Poly(A)- and Primer-Independent RNA Polymerase of Norovirus" Journal of Virology (2004) vol. 78 No. 8 pp. 3889-3896.*
Silverman, "The Organic Chemistry of Drug Design and Drug Action" Published 1992 by Academic Press, pp. 4-47 and 352-397.*
Burger's Medicinal Chemistry and Drug Discovery, Fifth Edition, vol. I: Principles nad Practice, edited by Manfred Wolff, published 1994 by Wiley-Interscience, pp. 975-977.*
Testa, B., "Prodrug Research: futile or fertile?" Biochemical pharmacology (2004) vol. 68 pp. 2097-2106.*
Stella, V. J., "Prodrugs as therapeutics" Expert Opinion on Therapeutic Patents (2004) vol. 14 No. 3 pp. 277-280.*
Ettmayer et al., "Lessons Learned from Marketed and Investigational Prodrugs" Journal of Medicinal Chemistry (2004) vol. 46 No. 10 pp. 2393-2404.*
Ferrer-Orta et al., "A comparison of viral RNA-dependent RNA polymerases" Current Opinion in Structural Biology (2006) vol. 16 pp. 27-34.*
Crotty et al., "Ribavirin's antiviral mechanism of action: lethal mutagenesis?" Journal of Molecular Medicine (2002) vol. 80 pp. 86-95.*
Clark, J. et al., "Synthesis and antiviral activity of 20-deoxy-20-fluoro-20-C-methyl purine nucleosides as inhibitors of hepatitis C virus", "Bioorganic & Medicinal Chemistry Letters", 2006, pp. 1712-1715, vol. 16.
Klumpp, K. et al, "The Novel Nucleoside Analog R1479 (4'-Azidocytidine) is a Potent Inhibitor of NS5B-dependent RNA Synthesis and Hepatitis", "The Journal of Biological Chemistry", Feb. 17, 2006, pp. 3793-3799, vol. 281, No. 7.
Perigaud, C. et al., "Nucleoside Analogues As Chemotherapeutic Agents: A Review", "Nucleosides and Nucleotides", 1992, pp. 903-945, vol. 11, No. 2-4.
Zamyatkin, D. et al., "Structural Insights into Mechanisms of Catalysis and Inhibition in Norwalk Virus Polymerase", "The Journal of Biological Chemistry", Mar. 21, 2008, pp. 7705-7712, vol. 283, No. 12.

* cited by examiner

*Primary Examiner* — Eric S Olson
(74) *Attorney, Agent, or Firm* — Hultquist, PLLC; David Bradin

(57) ABSTRACT

A method and composition for treating a host infected with a Caliciviridae virus, such as a Norovirus, comprising administering an effective treatment amount of a described modified nucleoside or a pharmaceutically acceptable salt thereof, is provided.

21 Claims, No Drawings

NUCLEOSIDE DERIVATIVES FOR TREATMENT OF *CALICIVIRIDAE* INFECTIONS, INCLUDING NOROVIRUS INFECTIONS

CROSS REFERENCE TO RELATED APPLICATION

This application claims priority under 35 U.S.C. §120 of U.S. Provisional Patent Application No. 61/045,064 filed Apr. 15, 2008 in the U.S. Patent and Trademark Office. The disclosure of the foregoing application is hereby incorporated herein in its respective entirety, for all purposes.

FIELD OF INVENTION

The invention is in the area of antiviral nucleoside analogs specifically where the analogs are used for treating a Caliciviridae infection, such as a Norovirus infection or as a prophylactic treatment to inhibit Norovirus infection. The invention provides chemical compounds, pharmaceutical compositions of these compounds and methods of treatment as monotherapy or in combination with other treatments which are novel for Norovirus infections.

BACKGROUND OF THE INVENTION

Norovirus is one of four viral genera found in the non-enveloped positive strand RNA family Caliciviridae. The other three species in Caliciviridae are Lagovirus, Vesivirus, and Sapovirus. Sapovirus is the only member of the genus other than Norovirus which utilizes humans as hosts. The Norovirus genome is approximately 7.56 kb with three open reading frames (ORFs). The first ORF codes for nonstructural proteins including a helicase, a protease, and an RNA directed RNA polymerase (RDRP) all of which are required for replication of the virus. The remaining two ORFs code for Capsid proteins (Jiang, X. (1993) Virology 195(1):51-61). The numerous strains of Norovirus have been classified into 5 genogroups of which I, II, and IV infect humans (Zheng, D. P., et al. (2006) Virology 346(2):312-323) and are estimated by the CDC to cause approximately 23 million gastroenteritis cases, corresponding to 40% of foodborne illness each year in the US (Mead P. S. (1999) Emerg. Infect. Dis. 5(5):607-625).

Common symptoms are vomiting, diarrhea, and intestinal cramps. Vomiting is the most common symptom in children, while diarrhea is more common in infected adults. Dehydration is a significant concern. The loss of life due to this virus is about 300 patients per year in the United States, and these deaths are usually among patients with a weak immune system (Centers for Disease Control and Prevention. "Norwalk-like viruses:" public health consequences and outbreak management. MMWR 2001; 50 (No. RR-9):3). The incubation period from exposure to full infection is typically 24 to 48 hrs with approximately 30% of infected individuals showing no symptoms. Symptoms generally persist for 24 to 60 hrs (Adler, J. L. and Zickl, R., J. (1969) Infect. Dis. 119:668-673). Viral shedding may last for 2 weeks or longer following the infection, however, it is not clear whether this virus is infectious.

Norovirus is transmitted primarily by the fecal-oral route through contaminated food or water, person to person contact, aerosols of vomit or stool samples. Viral titers in stool samples can reach $10^6$ to $10^7$ particles per mL, and particles are stable to temperatures of 0° C. (32° F.) to 60° C. (140° F.) (Duizer, E. et al., (2004) Appl. Environ. Microbiol. 70(8); 4538-4543). The virus is highly infectious, and various sources suggest infection may require inoculation of as few as 10 to 100 viral particles (Centers for Disease Control and Prevention. "Norwalk-like viruses:" public health consequences and outbreak management. MMR 2001; 50(No. RR-9):3-6). This leads to epidemics in schools, nursing homes, cruise ships, hospitals, or other locations where people congregate.

Norovirus is named for Norwalk-like viruses, a name derived from an outbreak at a school in Norwalk, Ohio in 1968. The viral particle responsible for the Norwalk illness was identified in 1972 by immune electron microscopy following passage of rectal swab filtrates through three sets of human volunteers (Kapikian, A. Z. et al. (1972) J. Virol. 10:1075-1081). In following years, the virus was called small round structured virus due to its electron microscopic image, calicivirus since it a member of the Caliciviridae family, and/or probably most commonly Norwalk-like virus after the originally isolated strain. Common names for the virus include winter vomiting virus, stomach flu, food poisoning, and viral gastroenteritis. While the outcome of infection is generally non-life threatening, the cost of loss of use of facilities and loss of productivity is great, consequently, a therapy for treatment of Norovirus infection in humans would be very desirable.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473). Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads, and at least initially seems as though it would be difficult to screen a meaningful number of compounds with this system. Eventually the infectivity assay may be useful for screening entry inhibitors. Other groups, such as Ligocyte Pharmaceuticals, Inc. (http://www.ligocyte.com/) have focused on trying to develop a vaccine against Noroviruses, however, these efforts have not yet been successful and may prove difficult as has often been the case in viral systems where low replicase fidelity is an evolutionary benefit.

It would be advantageous to provide compounds, compositions and methods for treating Norovirus infections. The present invention provides such compounds, compositions and methods.

SUMMARY OF THE INVENTION

Compounds, methods, and compositions for treating Norovirus infection in humans are disclosed. The compounds are substituted nucleosides of the Formulas (I)-(XIX), or a pharmaceutically acceptable salt or prodrug thereof, which demonstrate antiviral activity against a Norovirus infection. These compounds or formulations thereof can also be used prophylactically to prevent or decrease the spread of illness due to Norovirus infection.

The present invention will be better understood with reference to the following detailed description.

DETAILED DESCRIPTION

Compounds, methods, and compositions for treating Norovirus infection in humans are disclosed. The compounds are substituted nucleosides of the Formulas (I)-(XIX), or a pharmaceutically acceptable salt or prodrug thereof, which demonstrate antiviral activity against a Norovirus infection. While not wishing to be bound to a particular theory, it is believed that the compounds described herein are useful in inhibiting the viral polymerase and/or viral helicase as their mode of action.

As with Hepatitis C replicons, Norovirus replicons require viral helicase, protease, and polymerase to be functional in order for replication of the replicon to occur. The replicons can be used in high throughput assays, which evaluate whether a compound to be screened for activity inhibits the ability of Norovirus helicase, protease, and/or polymerase to function, as evidenced by an inhibition of replication of the replicon.

The present invention will be better understood with reference to the following definitions:

DEFINITIONS

Definitions The term "alkyl", as used herein, unless otherwise specified, refers to a saturated straight, branched, or cyclic, primary, secondary, or tertiary hydrocarbon of typically $C_1$ to $C_{10}$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, butyl, isobutyl, secbutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups, and particularly includes halogenated alkyl groups, and even more particularly fluorinated alkyl groups. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference.

The term "lower alkyl", as used herein, and unless otherwise specified, refers to a $C_1$ to $C_4$ saturated straight, branched, or if appropriate, a cyclic (for example, cyclopropyl) alkyl group, including both substituted and unsubstituted moieties.

The term "alkylamino" or "arylamino" refers to an amino group that has one or two alkyl or aryl substituents, respectively. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl", as used herein, and unless otherwise specified, refers to phenyl, biphenyl, or naphthyl, and preferably phenyl. The term includes both substituted and unsubstituted moieties. The aryl group can be substituted with any described moiety, including, but not limited to, one or more moieties selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

The term "alkaryl" or "alkylaryl" refers to an alkyl group with an aryl substituent.

The term aralkyl or arylalkyl refers to an aryl group with an alkyl substituent.

The term "halo", as used herein, includes chloro, bromo, iodo, and fluoro.

The term "purine" or "pyrimidine" base includes, but is not limited to, adenine, N6-alkylpurines, N6-acylpurines (wherein acyl is C(O) (alkyl, aryl, alkylaryl, or arylalkyl), N6-benzylpurine, N6-halopurine, N6-vinylpurine, N6-acetylenic purine, N6-acyl purine, N6-hydroxyalkyl purine, N6-alkylaminopurine, N6-thioalkyl purine, N2-alkylpurines, N2-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, C5-alkylpyrimidines, C5-benzylpyrimidines, C5-halopyrimidines, C5-vinylpyrimidine, C5-acetylenic pyrimidine, C5-acyl pyrimidine, C5-hydroxyalkyl purine, C5-amidopyrimidine, C5-cyanopyrimidine, C5-iodopyrimidine, C6-iodo-pyrimidine, C5-Br-vinyl pyrimidine, C6-Br-vinyl pyrimidine, C5-nitropyrimidine, C5-amino-pyrimidine, N2-alkylpurines, N2-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" refers to a group of the formula C(O)R', wherein R' is an straight, branched, or cyclic alkyl (including lower alkyl), amino acid, aryl including phenyl, alkaryl, aralkyl including benzyl, alkoxyalkyl including methoxymethyl, aryloxyalkyl such as phenoxymethyl; or substituted alkyl (including lower alkyl), aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxy-trityl, substituted benzyl, alkaryl, aralkyl including benzyl, alkoxyalkyl including methoxymethyl, aryloxyalkyl such as phenoxymethyl. Aryl groups in the esters optimally comprise a phenyl group. In particular, acyl groups include acetyl, trifluoroacetyl, methylacetyl, cyclopropylacetyl, cyclopropyl carboxy, propionyl, butyryl, hexanoyl, heptanoyl, octanoyl, neoheptanoyl, phenylacetyl, 2-acetoxy-2-phenylacetyl, diphenylacetyl, a-methoxy-a-trifluoromethyl-phenylacetyl, bromoacetyl, 2-nitro-benzeneacetyl, 4-chloro-benzeneacetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, methoxyacetyl, 2-thiopheneacetyl, chlorosulfonylacetyl, 3-methoxyphenylacetyl, phenoxyacetyl, tert-butylacetyl, trichloroacetyl, monochloro-acetyl, dichloroacetyl, 7H-dodecafluoro-heptanoyl, perfluoro-heptanoyl, 7H-dodeca-fluoroheptanoyl, 7-chlorododecafluoro-heptanoyl, 7-chloro-dodecafluoroheptanoyl, 7H-dodecafluoroheptanoyl, 7H-dodeca-fluoroheptanoyl, nona-fluoro-3,6-dioxa-heptanoyl, nonafluoro-3,6-dioxaheptanoyl, perfluoroheptanoyl, methoxybenzoyl, methyl 3-amino-5-phenylthiophene-2-carboxyl, 3,6- dichloro-2-methoxy-benzoyl, 4-(1,1,2,2-tetrafluoro-ethoxy)-benzoyl, 2-bromo-propionyl, omega-aminocapryl, decanoyl, n-pentadecanoyl, stearyl, 3-cyclopentyl-propionyl, 1-benzene-carboxyl, O-acetylmandelyl, pivaloyl acetyl, 1-adamantane-carboxyl, cyclohexane-carboxyl, 2,6-pyridinedicarboxyl, cyclopropane-carboxyl, cyclobutane-carboxyl, perfluorocyclohexyl carboxyl, 4-methylbenzoyl, chloromethyl isoxazolyl carbonyl, perfluorocyclohexyl carboxyl, crotonyl, 1-methyl-1H-indazole-3-carbonyl, 2-propenyl, isovaleryl, 1-pyrrolidinecarbonyl, 4-phenylbenzoyl. When the term acyl is used, it is meant to be a specific and independent disclosure of acetyl, trifluoroacetyl, methylacetyl, cyclopropylacetyl, propionyl, butyryl, hexanoyl, heptanoyl, octanoyl, neo-heptanoyl, phenylacetyl, diphenylacetyl, a-trifluoromethyl-phenylacetyl, bromoacetyl, 4-chloro-benzene-acetyl, 2-chloro-2,2-diphenylacetyl, 2-chloro-2-phenylacetyl, trimethylacetyl, chlorodifluoroacetyl, perfluoroacetyl, fluoroacetyl, bromodifluoroacetyl, 2-thiopheneacetyl, tert-butylacetyl, trichloroacetyl, monochloro-acetyl, dichloroacetyl, methoxybenzoyl, 2-bromo-propionyl, decanoyl, n-pentadecanoyl, stearyl, 3-cyclopentyl-propionyl, 1-benzene-carboxyl, pivaloyl acetyl, 1-adamantane-carboxyl, cyclohexane-carboxyl, 2,6-pyridinedicarboxyl, cyclopropane-carboxyl, cyclobutane-carboxyl, 4-methylbenzoyl, crotonyl, 1-methyl-1H-indazole-3-carbonyl, 2-propenyl, isovaleryl, 4-phenylbenzoyl.

The term "amino acid" includes naturally-occurring and synthetic α, β, γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration.

Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, p-argininyl or β-histidinyl. When the term amino acid is used, it is considered to be a specific and independent disclosure of each of the esters of α, β, γ, or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

As used herein, the term "substantially free of" or "substantially in the absence of" refers to a nucleoside composition that includes at least 85 or 90% by weight, preferably 95%, 98%, 99% or 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85%, 90%, 95%, 98%, 99%, or 100% by weight, of the nucleoside, the remainder comprising other chemical species or enantiomers.

The term "host", as used herein, refers to an unicellular or multicellular organism in which the virus can replicate, including cell lines and animals, and preferably a human.

Alternatively, the host can be carrying a part of the Norovirus viral genome, whose replication or function can be altered by the compounds of the present invention. The term host specifically refers to infected cells, cells transfected with all or part of the Norovirus genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against a Norovirus, or are metabolized to a compound that exhibits such activity.

I. Compounds

The compounds generally have the following formulas:

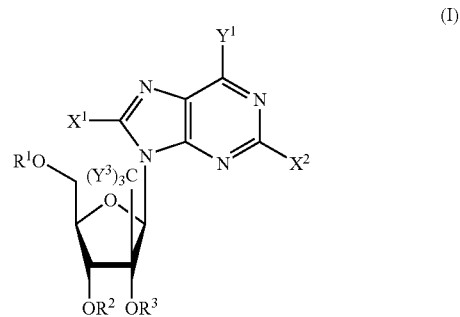

(I)

or a pharmaceutically acceptable salt thereof,
wherein:
$R^1$, $R^2$, and $R^3$ are independently H; phosphate; straight chained, branched or cyclic alkyl; acyl; CO-alkyl, CO-aryl, CO-alkoxyalkyl, CO-aryloxyalkyl, CO-substituted aryl, sulfonate ester; benzyl, wherein the phenyl group is optionally substituted with one or more substituents; alkylsulfonyl; arylsulfonyl; aralkylsulfonyl; a lipid; an amino acid; an amino acid residue; a carbohydrate; a peptide; cholesterol; or pharmaceutically acceptable leaving group which when administered in vivo is capable of providing a compound wherein $R^1$, $R^2$, and/or $R^3$ is independently H or phosphate;
wherein at least one of $R^2$ and $R^3$ is not hydrogen; and
wherein:
$Y^1$ is hydrogen, bromo, chloro, fluoro, iodo, CN, OH, $OR^4$, $NH_2$, $NHR^4$, $NR^4R^5$, SH or $SR^4$;
$X^1$ is a straight chained, branched or cyclic optionally substituted alkyl, $CH_3$, $CF_3$, $C(Y^3)_3$, 2-Br-ethyl, $CH_2F$, CH$_2$Cl, CH$_2$CF$_3$, CF$_2$CF$_3$, C(Y$^3$)$_2$C(Y$^3$)$_3$, CH$_2$OH, optionally substituted alkenyl, optionally substituted alkynyl, COOH, COOR$^4$, COO-alkyl, COO-aryl, CO-Oalkoxyalkyl, CONH$_2$, CONHR$^4$, CON(R$^4$)$_2$, chloro, bromo, fluoro, iodo, CN, N$_3$, OH, OR$^4$, NH$_2$, NHR$^4$. NR$^4$R$^5$, SH or SR$^5$; and X$^2$ is H, straight chained, branched or cyclic optionally substituted alkyl, CH$_3$, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, CH$_2$OH, optionally substituted alkenyl, optionally substituted alkynyl, COOH, COOR$^4$, COO-aryl, CO-Oalkoxyalkyl, CONH$_2$, CONHR$^4$, CON(R$^4$)$_2$, chloro, bromo, fluoro, iodo, CN, N$_3$, OH, OR$^4$, NH$_2$, NHR$^4$, NR$^4$R$^5$, SH or SR$^5$; and wherein each Y$^3$ is independently H, F, Cl, Br or I; and each R$^4$ and R$^5$ is independently hydrogen, acyl, alkyl, lower alkyl, alkenyl, alkynyl, or cycloalkyl;

A compound of Formula (II):

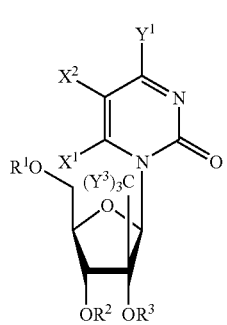

(II)

or a pharmaceutically acceptable salt thereof,
wherein:

R$^1$, R$^2$, and R$^3$ are independently H; phosphate; straight chained, branched or cyclic alkyl; acyl; CO-alkyl, CO-aryl, CO-alkoxyalkyl, CO-aryloxyalkyl, CO-substituted aryl, sulfonate ester; benzyl, wherein the phenyl group is optionally substituted with one or more substituents; alkylsulfonyl; arylsulfonyl; aralkylsulfonyl; a lipid; an amino acid; an amino acid residue; a carbohydrate; a peptide; cholesterol; or pharmaceutically acceptable leaving group which when administered in vivo is capable of providing a compound wherein R$^1$, R$^2$, and/or R$^3$ is independently H or phosphate;

wherein at least one of R$^2$ and R$^3$ is not hydrogen; and
wherein:

Y$^1$ is hydrogen, bromo, chloro, fluoro, iodo, CN, OH, OR$^4$, NH$_2$, NHR$^4$, NR$^4$R$^5$, SH or SR$^4$;

X$^1$ is a straight chained, branched or cyclic optionally substituted alkyl, CH$_3$, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, CH$_2$OH, optionally substituted alkenyl, optionally substituted alkynyl, COOH, COOR$^4$-alkyl, COO-aryl, CO-Oalkoxyalkyl, CONH$_2$, CONHR$^4$, CON(R$^4$)$_2$, chloro, bromo, fluoro, iodo, CN, N$_3$, OH, OR$^4$, NH$_2$, NHR$^4$, NR$^4$R$^5$, SH, or SR$^5$; and X$^2$ is H, straight chained, branched or cyclic optionally substituted alkyl, CH$_3$, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, CH$_2$OH, optionally substituted alkenyl, optionally substituted alkynyl, COOH, COOR$^4$, COO-alkyl, COO-aryl, CO-Oalkoxyalkyl, CONH$_2$, CONHR$^4$, CON(R$^4$)$_2$, chloro, bromo, fluoro, iodo, CN, N$_3$, OH, OR$^4$, NH$_2$, NHR$^4$, NR$^4$R$^5$, SH, or SR$^5$; and wherein each Y$^3$ is independently H, F, Cl, Br, or I; and each R$^4$ and R$^5$ is independently hydrogen, acyl, alkyl, lower alkyl, alkenyl, alkynyl, or cycloalkyl.

A compound of Formula (III), (IV), or (V):

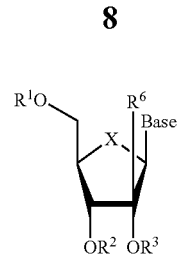

(III)

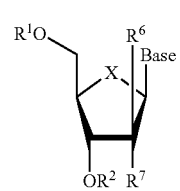

(IV)

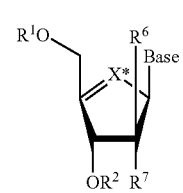

(V)

or a pharmaceutically acceptable salt thereof,
wherein:

R$^1$, R$^2$, and R$^3$ are independently H; phosphate; straight chained, branched or cyclic alkyl; acyl; CO-alkyl, CO-aryl, CO-alkoxyalkyl, CO-aryloxyalkyl, CO-substituted aryl, sulfonate ester; benzyl, wherein the phenyl group is optionally substituted with one or more substituents; alkylsulfonyl; arylsulfonyl; aralkylsulfonyl; a lipid; an amino acid; an amino acid residue; a carbohydrate; a peptide; cholesterol; or pharmaceutically acceptable leaving group which when administered in vivo is capable of providing a compound wherein R$^1$, R$^2$, and/or R$^3$ is independently H or phosphate;

wherein at least one of R$^2$ and R$^3$ is not hydrogen; and
wherein:

Base is selected from the group consisting of

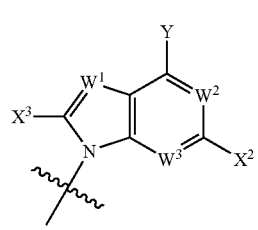

(A)

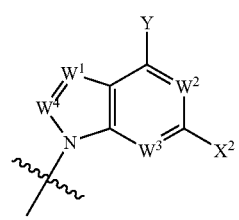

(B)

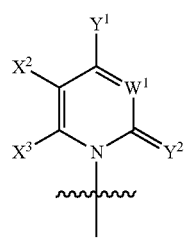 (C)
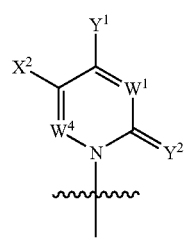 (D)
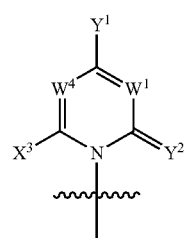 (E)
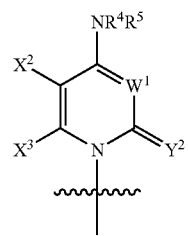 (F)
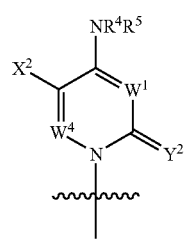 (G)
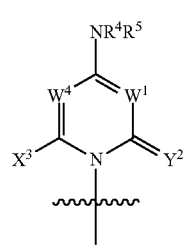 (H)
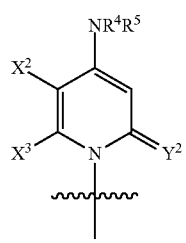 (I)
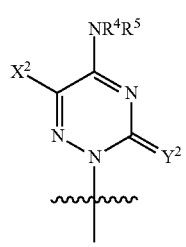 (J)
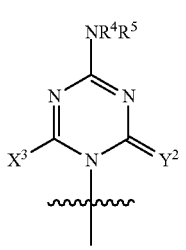 (K)
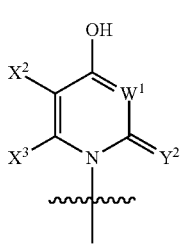 (L)
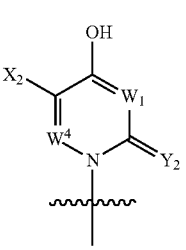 (M)
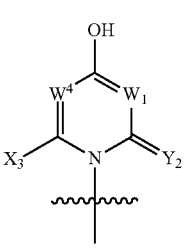 (N)

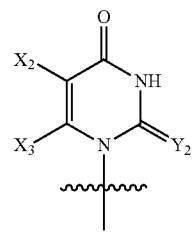 (O)
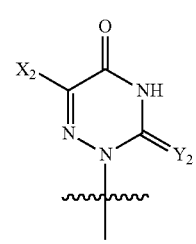 (P)
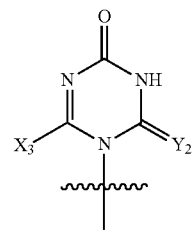 (Q)
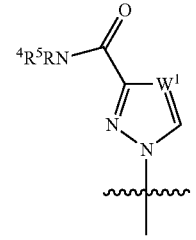 (R)
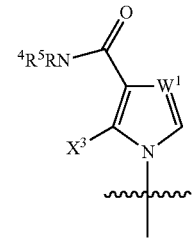 (S)
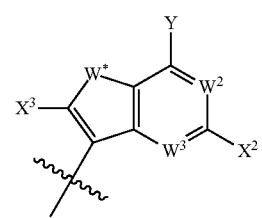 (T)
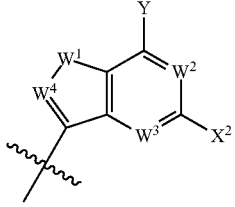 (U)
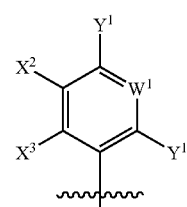 (V)
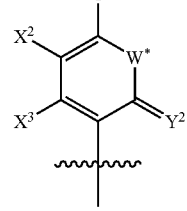 (W)
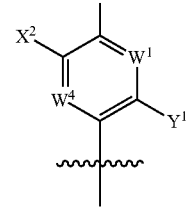 (X)
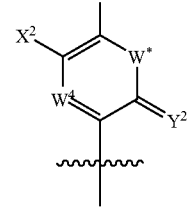 (Y)
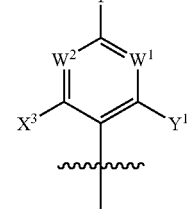 (Z)
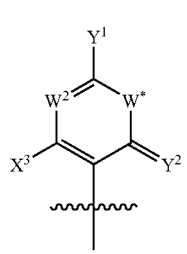 (BA)

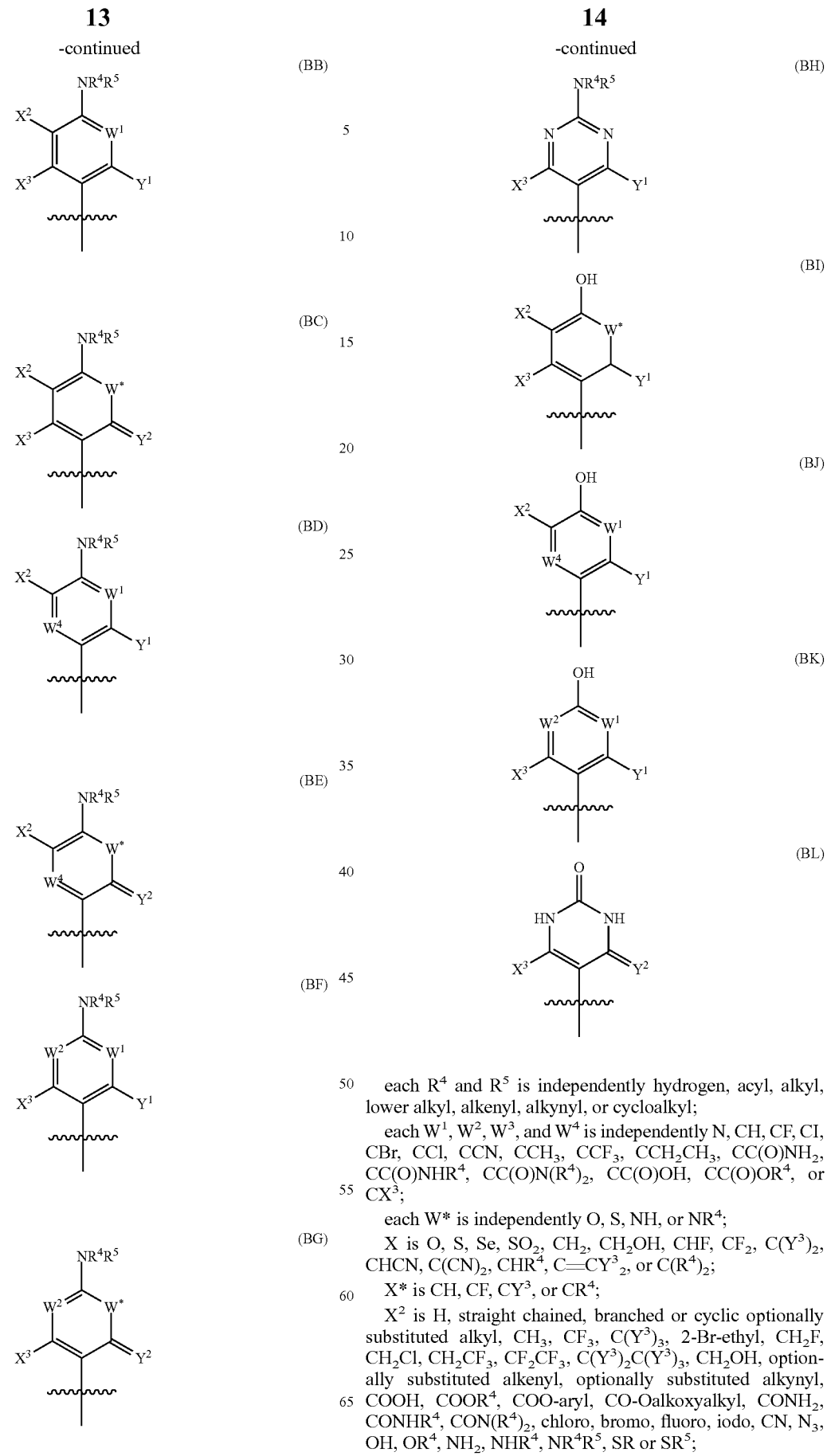

each $R^4$ and $R^5$ is independently hydrogen, acyl, alkyl, lower alkyl, alkenyl, alkynyl, or cycloalkyl;

each $W^1$, $W^2$, $W^3$, and $W^4$ is independently N, CH, CF, Cl, CBr, CCl, CCN, $CCH_3$, $CCF_3$, $CCH_2CH_3$, $CC(O)NH_2$, $CC(O)NHR^4$, $CC(O)N(R^4)_2$, $CC(O)OH$, $CC(O)OR^4$, or $CX^3$;

each $W^*$ is independently O, S, NH, or $NR^4$;

X is O, S, Se, $SO_2$, $CH_2$, $CH_2OH$, CHF, $CF_2$, $C(Y^3)_2$, CHCN, $C(CN)_2$, $CHR^4$, $C=CY^3{}_2$, or $C(R^4)_2$;

$X^*$ is CH, CF, $CY^3$, or $CR^4$;

$X^2$ is H, straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-aryl, CO-Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SR or $SR^5$;

each $X^3$ is independently a straight chained, branched or cyclic optionally substituted alkyl, $CH_3$, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, $N_3$, CN, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, OH, OR$^4$, —O(acyl), —O(lower acyl), —O(alkyl), —O(lower alkyl), —O(alkenyl), —O(alkynyl), —O(aralkyl), —O(cycloalkyl), S(acyl), —S(lower acyl), —S(R$^4$), —S(lower alkyl), —S(alkenyl), —S(alkynyl), —S(aralkyl), —S(cycloalkyl), chloro, bromo, fluoro, iodo, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), or —N(acyl)$_2$;

each Y is independently selected from the group consisting of H, optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3,CF_2CF_3$, $CH_2CO_2R$, $(CH_2)_mCOOH$, $(CH_2)_mCOOR$, $(CH_2)_mCONH_2$, $(CH_2)_mCONR_2$, and $(CH_2)_mCONHR$;

R is H, alkyl or acyl;

$Y^1$ is hydrogen, bromo, chloro, fluoro, iodo, CN, OH, OR$^4$, NH$_2$, NHR$^4$, NR$^4$R$^5$, SH or SR$^4$;

each $Y^2$ is independently O, S, Se, NH, or NR$^4$; and each $Y^3$ is independently H, F, Cl, Br, or I;

each $R^6$ is independently H, F, Cl, Br, I, an optionally substituted alkyl, $CH_3$, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, or cyano;

each $R^7$ is independently OH, OR$^2$, optionally substituted alkyl, $CH_3$, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle, optionally substituted heterocycle, optionally substituted heteroaryl, —CH$_2$C(O)OH, —CH$_2$C(O)OR$^4$, CH$_2$C(O)O(lower alkyl), —CH$_2$C(O)SH, —CH$_2$C(O)SR$^4$, —CR$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, (CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl), azido, cyano, SCN, OCN, NCO, F, Cl, Br, or I;

alternatively, $R^6$ and $R^7$ can come together to form a spiro compound selected from the group consisting of optionally substituted carbocycle or optionally substituted heterocycle; and each m is independently 0, 1, or 2.

A compound of Formula (VI) or (VII):

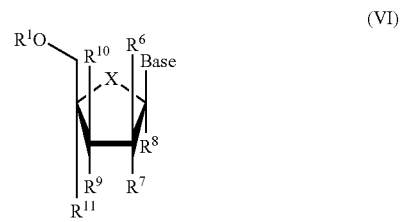

(VI)

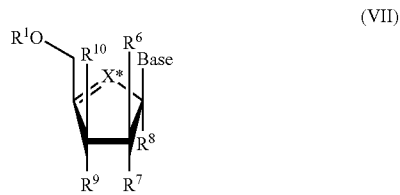

(VII)

or a pharmaceutically acceptable salt thereof, wherein:

$R^1$ is H; phosphate; straight chained, branched or cyclic alkyl; acyl; CO-alkyl; CO-aryl; CO-alkoxyalkyl; CO-aryloxyalkyl; CO-substituted aryl; sulfonate ester; benzyl, wherein the phenyl group is optionally substituted with one or more substituents; alkylsulfonyl; arylsulfonyl; aralkylsulfonyl; a lipid; an amino acid; an amino acid residue; a carbohydrate; a peptide; cholesterol; or pharmaceutically acceptable leaving group which when administered in vivo is capable of providing a compound wherein $R^1$ is H or phosphate; and wherein:

Base is selected from the group consisting of

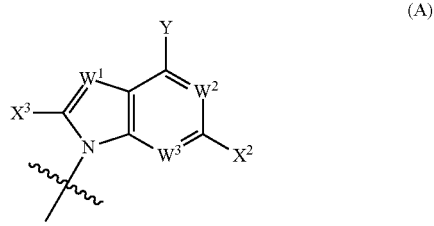

(A)

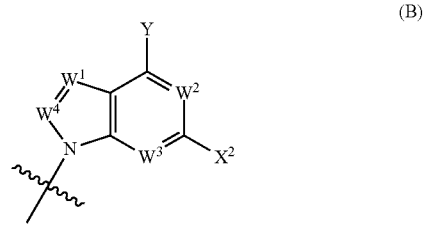

(B)

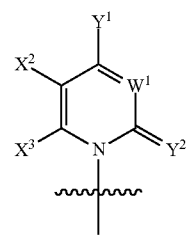 (C)
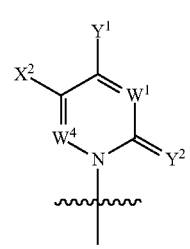 (D)
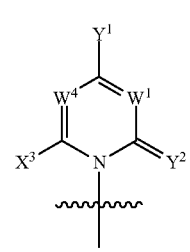 (E)
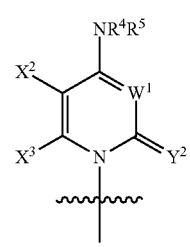 (F)
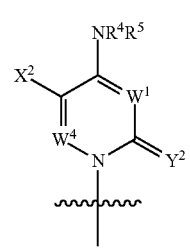 (G)
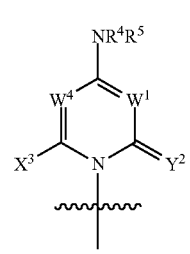 (H)
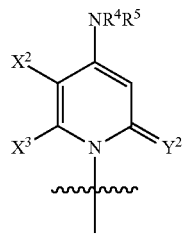 (I)
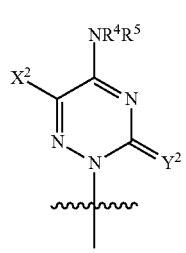 (J)
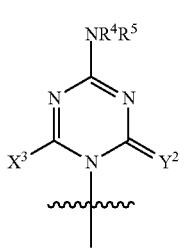 (K)
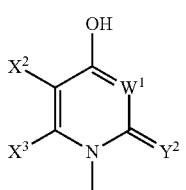 (L)
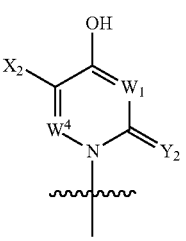 (M)
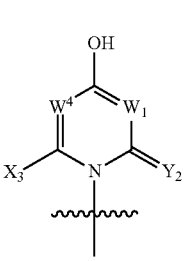 (N)

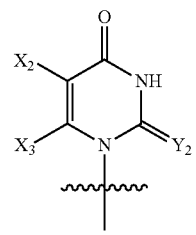 (O)
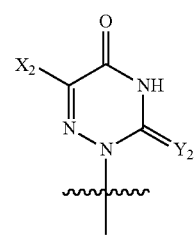 (P)
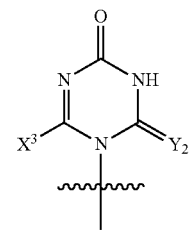 (Q)
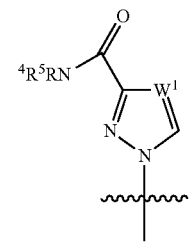 (R)
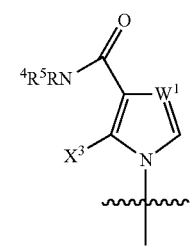 (S)
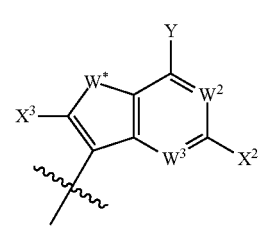 (T)
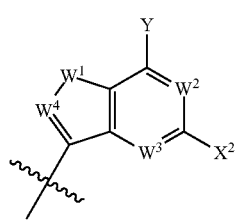 (U)
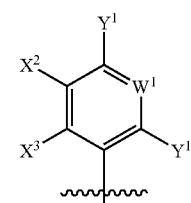 (V)
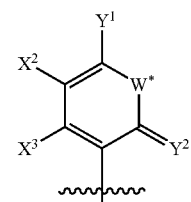 (W)
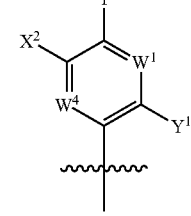 (X)
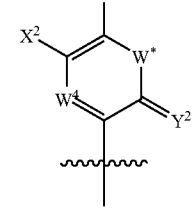 (Y)
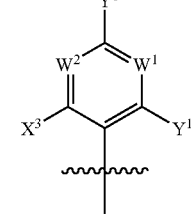 (Z)
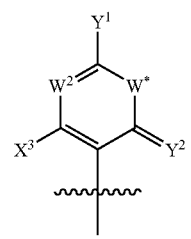 (BA)

(BB) 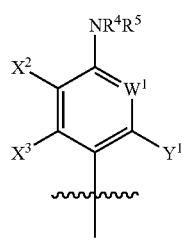

(BC) 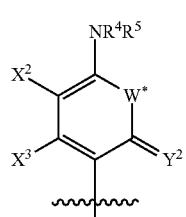

(BD) 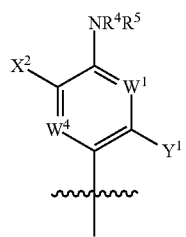

(BE) 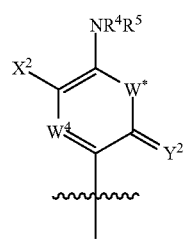

(BF) 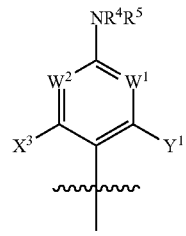

(BG) 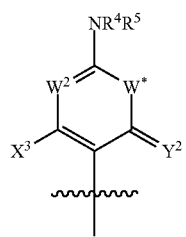

(BH) 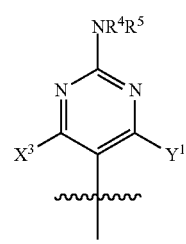

(BI) 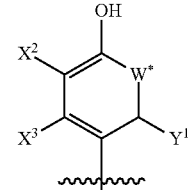

(BJ) 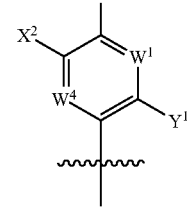

(BK) 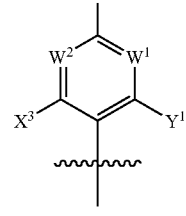

(BL) 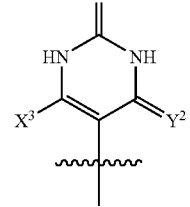

each $R^4$ and $R^5$ is independently hydrogen, acyl, alkyl, lower alkyl, alkenyl, alkynyl, or cycloalkyl; each $W^1$, $W^2$, $W^3$, and $W^4$ is independently N, CH, CF, Cl, CBr, CCl, CCN, $CCH_3$, $CCF_3$, $CCH_2CH_3$, $CC(O)NH_2$, $CC(O)NHR^4$, $CC(O)N(R^4)_2$, $CC(O)OH$, $CC(O)OR^4$, or $CX^3$;

each $W^*$ is independently O, S, Se, NH, or $NR^4$;

X is O, S, $SO_2$, $CH_2$, $CH_2OH$, CHF, $CF_2$, $C(Y^3)_2$, CHCN, $C(CN)_2$, $CHR^4$, $C=CY^3_2$, or $C(R^4)_2$;

$X^*$ is CH, CF, $CY^3$, or $CR^4$;

$X^2$ is H, straight chained, branched, or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted alkenyl, optionally substituted alkynyl, COOH, $COOR^4$, COO-aryl, CO-Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH, or $SR^5$;

each $X^3$ is independently a straight chained, branched or cyclic optionally substituted alkyl, $CH_3$, $CH_2CN$, $CH_2N_3$, CH$_2$NH$_2$, CH$_2$NHCH$_3$, CH$_2$N(CH$_3$)$_2$, CH$_2$OH, halogenated alkyl, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, N$_3$, CN, —C(O)OH, —C(O)OR$^4$, —C(O)O (lower alkyl), —C(O)NH$_2$, —C(O)NHR$^4$, —C(O)NH(lower alkyl), —C(O)N(R$^4$)$_2$, —C(O)N(lower alkyl)$_2$, OH, OR$^4$, —O(acyl), —O(lower acyl), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), chloro, bromo, fluoro, iodo, NH$_2$, —NH(lower alkyl), —NHR$^4$, —NR$^4$R$^5$, —NH(acyl), —N(lower alkyl)$_2$, —NH (alkenyl), —NH(alkynyl), —NH(aralkyl), —NH(cycloalkyl), or —N(acyl)$_2$;

each Y is independently selected from the group consisting of H, optionally substituted lower alkyl, cycloalkyl, alkenyl, alkynyl, CH$_2$OH, CH$_2$NH$_2$, CH$_2$NHCH$_3$, CH$_2$N(CH$_3$)$_2$, CH$_2$F, CH$_2$Cl, CH$_2$N$_3$, CH$_2$CN, CH$_2$CF$_3$, CF$_3$,CF$_2$CF$_3$, CH$_2$CO$_2$R, (CH$_2$)$_m$COOH, (CH$_2$)$_m$COOR, (CH$_2$)$_m$CONH$_2$, (CH$_2$)$_m$CONR$^2$, and (CH$_2$)$_m$CONHR;

R is H, alkyl or acyl;

Y$^1$ is hydrogen, bromo, chloro, fluoro, iodo, CN, OH, OR$^4$, NH$_2$, NHR$^4$, NR$^4$R$^5$, SH, or SR$^4$;

each Y$^2$ is independently O, S, Se, NH, or NR$^4$;

each Y$^3$ is independently H, F, Cl, Br, or I;

wherein for Base (B), W$^4$ cannot be CH if W$^1$, W$^2$, and W$^3$ are N;

wherein for Base (D), (G), and (M), W$^4$ cannot be CH if W$^1$ is N;

each R$^6$ is independently H, F, Cl, Br, I, an optionally substituted alkyl, CH$_3$, CH$_2$CN, CH$_2$N$_3$, CH$_2$NH$_2$, CH$_2$NHCH$_3$, CH$_2$N(CH$_3$), CH$_2$OH, halogenated alkyl, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, (CH$_2$)$_m$C(O)O(lower alkyl), —(CH$_2$)$_m$C(O)NH$_2$, —(CH$_2$)$_m$C(O)NHR$^4$—(CH$_2$)$_m$C(O)NH(lower alkyl), —(CH$_2$)$_m$C(O)N(R$^4$)$_2$, —(CH$_2$)$_m$C(O)N (lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$—C(O)N(lower alkyl)$_2$ or cyano;

each R$^7$ is independently OH, OR$^2$, optionally substituted alkyl, CH$_3$, CH$_2$CN, CH$_2$N$_3$, CH$_2$NH$_2$, CH$_2$NHCH$_3$, CH$_2$N (CH$_3$)$_2$, CH$_2$OH, halogenated alkyl, CF$_3$, C(Y$^3$)$_3$, 2Br-ethyl, CH$_2$F, CH$_2$Cl, CH$_2$CF$_3$, CF$_2$CF$_3$, C(Y$^3$)$_2$C(Y$^3$)$_3$, optionally substituted alkenyl, haloalkenyl, Br-vinyl, optionally substituted alkynyl, haloalkynyl, optionally substituted carbocycle, optionally substituted heterocycle, optionally substituted heteroaryl, —CH$_2$C(O)OH, —CH$_2$C(O)OR$^4$, —CH$_2$C(O)O (lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO, F, Cl, Br, or I;

alternatively, R$^6$ and R$^7$ can come together to form a spiro compound selected from the group consisting of optionally substituted carbocycle or optionally substituted heterocycle;

each R$^8$ and R$^{11}$ is independently hydrogen, an optionally substituted alkyl, CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl, CF$_3$, C(Y$^3$)$_3$, 2-Br-ethyl, CH$_2$F, CH$_2$Cl, CH$_2$CF$_3$, CF$_2$CF$_3$, C(Y$^3$)$_2$ C(Y$^3$)$_3$, optionally substituted alkenyl, haloalkenyl, Br-vinyl, optionally substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, azido, cyano, NH-acyl, or N(acyl)$_2$;

each R$^9$ and R$^{10}$ are independently hydrogen, OH, OR$^2$, optionally substituted alkyl, CH$_3$, CH$_2$CN, CH$_2$N$_3$, CH$_2$NH$_2$, CH$_2$NHCH$_3$, CH$_2$N(CH$_3$)$_2$, CH$_2$OH, halogenated alkyl CF$_3$, C(Y$^3$)$_3$, 2-Br-ethyl, CH$_2$F, CH$_2$Cl, CH$_2$CF$_3$, CF$_2$CF$_3$, C(Y$^3$)$_2$ C(Y$^3$)$_3$, optionally substituted alkenyl, haloalkenyl, Br-vinyl, optionally substituted alkynyl, haloalkynyl, optionally substituted carbocycle, optionally substituted heterocycle, optionally substituted heteroaryl, —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO, F, Cl, Br, or I;

each m is independently 0, 1, or 2; and alternatively, R$^6$ and R$^{10}$, R$^7$ and R$^9$, R$^8$ and R$^7$, or R$^9$ and R$^{11}$ can come together to form a bridged compound selected from the group consisting of optionally substituted carbocycle or optionally substituted heterocycle or alternatively, R$^6$ and R$^7$ or R$^9$ and R$^{10}$ can come together to form a spiro compound selected from the group consisting of optionally substituted carbocycle or optionally substituted heterocycle.

A compound of Formula (VIII), (IX), or (X):

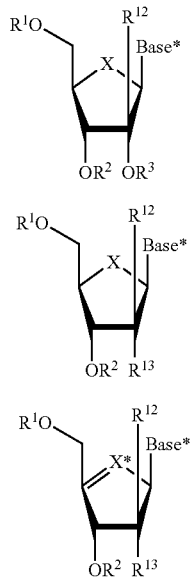

(VIII)

(IX)

(X)

or a pharmaceutically acceptable salt thereof, wherein:

wherein $R^1$, $R^2$, and $R^3$ are independently H; phosphate; straight chained, branched or cyclic alkyl; acyl; CO-alkyl; CO-aryl; CO-alkoxyalkyl; CO-aryloxyalkyl; CO-substituted aryl; sulfonate ester; benzyl, wherein the phenyl group is optionally substituted with one or more substituents; alkylsulfonyl; arylsulfonyl; aralkylsulfonyl; a lipid; an amino acid; an amino acid residue; a carbohydrate; a peptide; cholesterol; or pharmaceutically acceptable leaving group which when administered in vivo is capable of providing a compound wherein $R^1$, $R^2$, and/or $R^3$ is independently H or phosphate;

wherein at least one of $R^2$ and $R^3$ is not hydrogen;

X is O, S, Se, $SO_2$, $CH_2$, $CH_2OH$, CHF, $CF_2$, $C(Y^3)_2$, CHCN, $C(CN)_2$, $CHR^4$, $C=CY^3{}_2$, or $C(R^4)_2$;

X* is CH, CF, $CY^3$, or $CR^4$;

each $Y^3$ is independently H, F, Cl, Br, or I;

each $R^4$ and $R^5$ is independently hydrogen, acyl, alkyl, lower alkyl, alkenyl, or cycloalkyl;

Base* is a purine or pyrimidine base;

each $R^{12}$ is independently H, F, Cl, Br, I, a substituted alkyl, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, —$CH_2C(O)OH$, —$CH_2C(O)OR^4$, —$CH_2C(O)O$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)NH_2$, —$(CH_2)_m$ $C(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —$C(O)OR^4$, —$C(O)NH_2$, —$C(O)NHR^4$, —C(O)NH(lower alkyl), —$C(O)N(R^4)_2$, —C(O)N(lower alkyl)$_2$;

each $R^{13}$ is independently H, F, Cl, Br, I, substituted alkyl, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, optionally substituted carbocycle, optionally substituted heterocycle, optionally substituted heteroaryl, —$CH_2C(O)OH$, —$CH_2C(O)OR^4$, —$CH_2C(O)O$(lower alkyl), —$CH_2C(O)SH$, —$CH_2C(O)SR^4$, —$CH_2C(O)S$(lower alkyl), —$CH_2C(O)NH_2$, —$CH_2C(O)NHR^4$, —$CH_2C(O)NH$(lower alkyl), —$CH_2C(O)N(R^4)_2$, —$CH_2C(O)N$(lower alkyl)$_2$, —$(CH_2)_mC(O)OH$, —$(CH_2)_mC(O)OR^4$, —$(CH_2)_mC(O)O$(lower alkyl), —$(CH_2)_mC(O)SH$, —$(CH_2)_mC(O)SR^4$, —$(CH_2)_mC(O)S$(lower alkyl), —$(CH_2)_mC(O)NH_2$, —$(CH_2)_mC(O)NHR^4$, —$(CH_2)_mC(O)NH$(lower alkyl), —$(CH_2)_mC(O)N(R^4)_2$, —$(CH_2)_mC(O)N$(lower alkyl)$_2$, —C(O)OH, —$C(O)OR^4$, —C(O)SH, —$C(O)SR^4$, —C(O)S(lower alkyl), —$C(O)NH_2$, —$C(O)NHR^4$, —C(O)NH(lower alkyl), —$C(O)N(R^4)_2$, —C(O)N(lower alkyl)$_2$, —$O(R^4)$, —O(alkynyl), —O(aralkyl), —O(cycloalkyl), S(acyl), —S(lower acyl), —$S(R^4)$, —S(lower alkyl), —S(alkenyl), —S(alkynyl), —S(aralkyl), —S(cycloalkyl), —$NHR^4$, —$NR^4R^5$, —NH(alkenyl), —NH(alkynyl), —NH(aralkyl), —NH(cycloalkyl), SCN, OCN, NCO, or fluoro;

alternatively, $R^{12}$ and $R^{13}$ can come together to form a spiro compound selected from the group consisting of optionally substituted carbocycle or optionally substituted heterocycle;

and each m is independently 0, 1, or 2.

A compound of Formula (XI) or (XII):

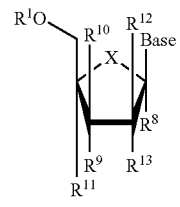

(XI)

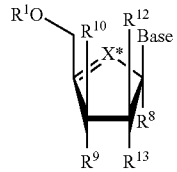

(XII)

or a pharmaceutically acceptable salt thereof, wherein:

$R^1$ is H; phosphate; straight chained, branched or cyclic alkyl; acyl; CO-alkyl; COaryl; CO-alkoxyalkyl; CO-aryloxyalkyl; CO-substituted aryl; sulfonate ester; benzyl, wherein the phenyl group is optionally substituted with one or more substituents; alkylsulfonyl; arylsulfonyl; aralkylsulfonyl; a lipid; an amino acid; an amino acid residue; a carbohydrate; a peptide; cholesterol; or pharmaceutically acceptable leaving group which when administered in vivo is capable of providing a compound wherein $R^1$ is H or phosphate;

Base is selected from the group consisting of

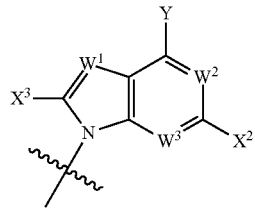

(A)

-continued
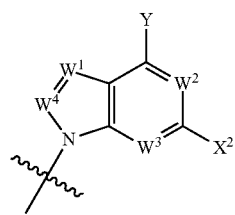
(B)
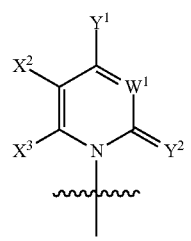
(C)
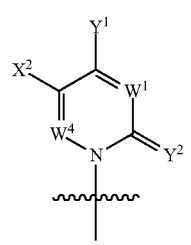
(D)
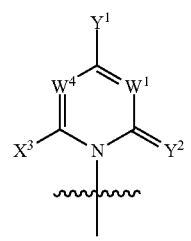
(E)
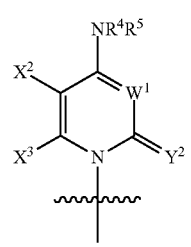
(F)
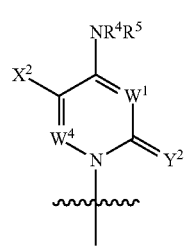
(G)
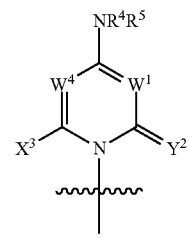
(H)
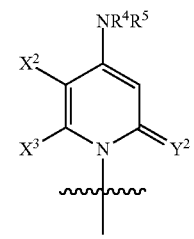
(I)
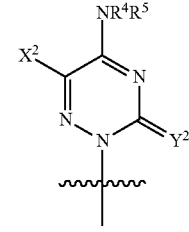
(J)
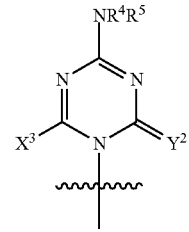
(K)
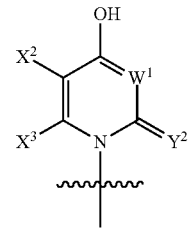
(L)
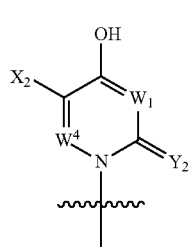
(M)

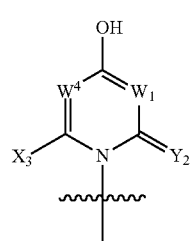 (N)
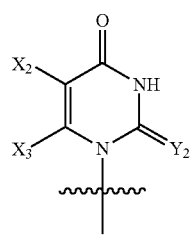 (O)
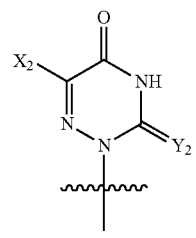 (P)
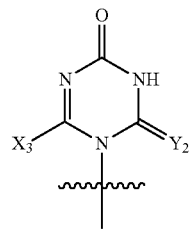 (Q)
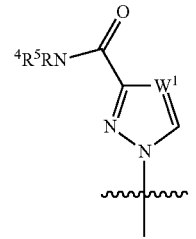 (R)
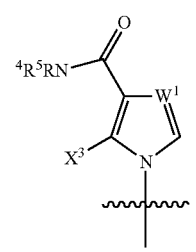 (S)
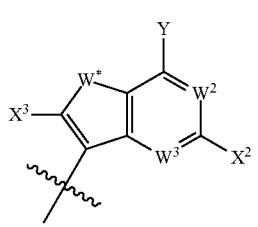 (T)
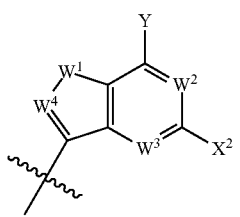 (U)
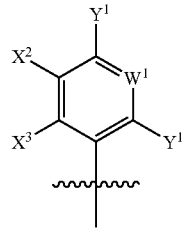 (V)
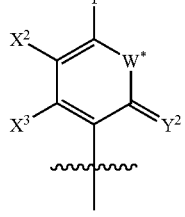 (W)
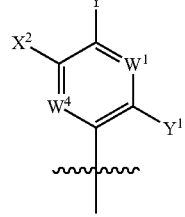 (X)
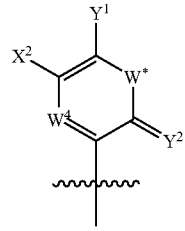 (Y)
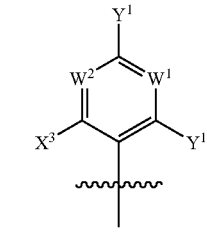 (Z)

(BA) 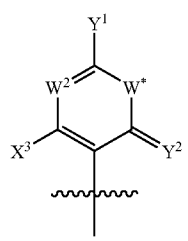
(BB) 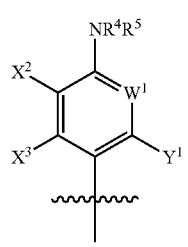
(BC) 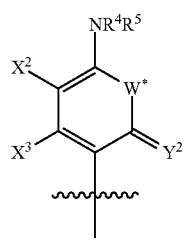
(BD) 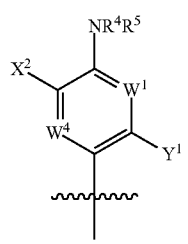
(BE) 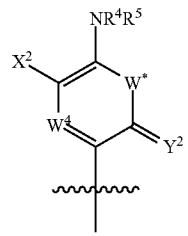
(BF) 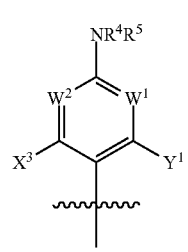
(BG) 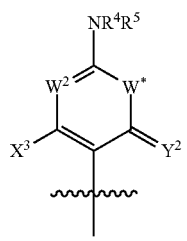
(BH) 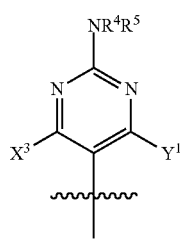
(BI) 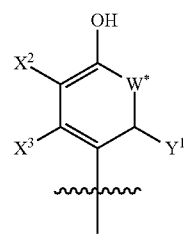
(BJ) 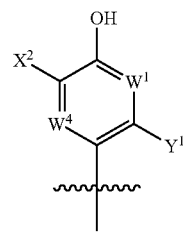
(BK) 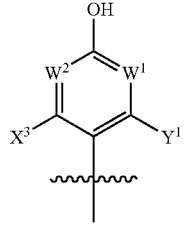
(BL) 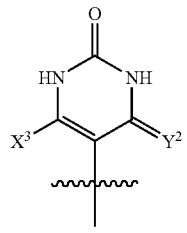
each $W^1$, $W^2$, $W^3$, and $W^4$ is independently N, CH, CF, Cl, CBr, CCl, CCN, CCH$_3$, CCF$_3$, CCH$_2$CH$_3$, CC(O)NH$_2$, CC(O)NHR$^4$, CC(O)N(R$^4$)$_2$, CC(O)OH, CC(O)OR$^4$, or CX$^3$;
each W* is independently O, S, Se, NH, or NR$^4$;
X is O, S, Se, SO$_2$, CH$_2$, CH$_2$OH, CHF, CF$_2$, C(Y$^3$)$_2$, CHCN, C(CN)$_2$, CHR$^4$, C=CY$^3$$_2$, or C(R$^4$)$_2$;
X* is CH, CF, CY$^3$, or CR$^4$;

$X^2$ is H, straight chained, branched or cyclic optionally substituted alkyl, $CH_3$, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, $CH_2OH$, optionally substituted, optionally substituted alkynyl, COOH, $COOR^4$, COO-alkyl, COO-aryl, CO-Oalkoxyalkyl, $CONH_2$, $CONHR^4$, $CON(R^4)_2$, chloro, bromo, fluoro, iodo, CN, $N_3$, OH, $OR^4$, $NH_2$, $NHR^4$, $NR^4R^5$, SH, or $SR^5$;

each $X^3$ is independently a straight chained, branched or cyclic optionally substituted alkyl, $CH_3$, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, $N_3$, CN, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, OH, OR$^4$, —O(acyl), —O(lower acyl), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), chloro, bromo, fluoro, iodo, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), or —N(acyl)$_2$;

each Y is independently selected from the group consisting of H, optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_mCOOH$, $(CH_2)_mCOOR$, $(CH_2)_mCONH_2$, $(CH_2)_mCONR_2$, and $(CH_2)_mCONHR$; R is H, alkyl, or acyl;

$Y^1$ is hydrogen, bromo, chloro, fluoro, iodo, CN, OH, $OR^4$, $NH_2$, $NHR^4$, $NR^4R^5$, SH, or $SR^4$;

each $Y^2$ is independently O, S, Se, NH, or $NR^4$;

each $Y^3$ is independently H, F, Cl, Br, or I;

each $R^4$ and $R^5$ is independently hydrogen, acyl, alkyl, lower alkyl, alkenyl, alkynyl, or cycloalkyl;

each $R^{12}$ is independently H, F, Cl, Br, I, a substituted alkyl, $CH_2CN$, $CH_2N_3$, $CH_2NH_2$, $CH_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)NH$_2$, —C(O)NHR$^4$, —C(O)NH(lower alkyl), —C(O)N(R$^4$)$_2$, or —C(O)N(lower alkyl)$_2$;

each $R^{13}$ is independently H, F, Cl, Br, I, a substituted alkyl, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, substituted alkenyl, haloalkenyl (but not Br-vinyl), substituted alkynyl, haloalkynyl, optionally substituted carbocycle, optionally substituted heterocycle, optionally substituted heteroaryl, —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(R$^4$), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), —NHR$^4$, —NR$^4$R$^5$, —NH(alkenyl), —NH(alkynyl), —NH(aralkyl), —NH(cycloalkyl), SCN, OCN, NCO, or fluoro; and alternatively, $R^{12}$ and $R^{13}$ can come together to form a spiro compound selected from the group consisting of optionally substituted carbocycle or optionally substituted heterocycle;

each $R^8$ and $R^{11}$ is independently hydrogen, an optionally substituted alkyl (including lower alkyl), $CH_3$, $CH_2CN$, $CH_2N_3$, $CH_2NH_2$, $CH_2NHCH_3$, $CH_2N(CH_3)_2$, $CH_2OH$, halogenated alkyl (including halogenated lower alkyl), $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, —CH$_2$C(O)OH, —CH$_2$C(O)OR$^4$, —CH$_2$C(O)O(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)NH$_2$, —C(O)NHR$^4$, —C(O)NH(lower alkyl), —C(O)N(R$^4$)$_2$, —C(O)N(lower alkyl)$_2$, cyano, NH-acyl, or N(acyl)$_2$;

each $R^9$ and $R^{10}$ are independently hydrogen, OH, $OR^2$, optionally substituted alkyl, $CH_3$, $CH_2CN$, $CH_2N_3$, $CH_2NH_2$, $CR_2NHCH_3$, $CH_2N(CH_3)_2$, $CH_2OH$, halogenated alkyl, $CF_3$, $C(Y^3)_3$, 2-Br-ethyl, $CH_2F$, $CH_2Cl$, $CH_2CF_3$, $CF_2CF_3$, $C(Y^3)_2C(Y^3)_3$, optionally substituted alkenyl, haloalkenyl, Br-vinyl, optionally substituted alkynyl, haloalkynyl, optionally substituted carbocycle, optionally substituted heterocycle, optionally substituted heteroaryl, —CH$_2$C(O)OH, —CH$_2$C(O)OR$^4$, —CH$_2$C(O)O(lower alkyl), —CH$_2$C(O)SH, —CH$_2$C(O)SR$^4$, —CH$_2$C(O)S(lower alkyl), —CH$_2$C(O)NH$_2$, —CH$_2$C(O)NHR$^4$, —CH$_2$C(O)NH(lower alkyl), —CH$_2$C(O)N(R$^4$)$_2$, —CH$_2$C(O)N(lower alkyl)$_2$, —(CH$_2$)$_m$C(O)OH, —(CH$_2$)$_m$C(O)OR$^4$, —(CH$_2$)$_m$C(O)O(lower alkyl), —(CH$_2$)$_m$C(O)SH, —(CH$_2$)$_m$C(O)SR$^4$, —(CH$_2$)$_m$C(O)S(lower alkyl), —(CH$_2$)$_m$C(O)NH$_2$, —(CH$_2$)$_m$C(O)NHR$^4$, —(CH$_2$)$_m$C(O)NH(lower alkyl), —(CH$_2$)$_m$C(O)N(R$^4$)$_2$, —(CH$_2$)$_m$C(O)N(lower alkyl)$_2$, —C(O)OH, —C(O)OR$^4$, —C(O)O(lower alkyl), —C(O)SH, —C(O)SR$^4$, —C(O)S(lower alkyl), —C(O)NH$_2$, —C(O)NHR$^4$, —C(O)NH(lower alkyl), —C(O)N(R$^4$)$_2$, —C(O)N(lower alkyl)$_2$, —O(acyl), —O(lower acyl), —O(R$^4$), —O(alkyl), —O(lower alkyl), —O(alkenyl), —O(alkynyl), —O(aralkyl), —O(cycloalkyl), —S(acyl), —S(lower acyl), —S(R$^4$), —S(lower alkyl), —S(alkenyl), —S(alkynyl), —S(aralkyl), —S(cycloalkyl), NO$_2$, NH$_2$, —NH(lower alkyl), —NHR$^4$, —NR$^4$R$^5$, —NH(acyl), —N(lower alkyl)$_2$, —NH(alkenyl), —NH(alkynyl), —NH(aralkyl), —NH(cycloalkyl), —N(acyl)$_2$, azido, cyano, SCN, OCN, NCO, F, Cl, Br, or I;

each m is independently 0, 1, or 2; and alternatively, $R^8$ and $R^{13}$, $R^9$ and $R^{13}$, $R^9$ and $R^{11}$, or $R^{10}$ and $R^{12}$ can come together to form a bridged compound selected from the group consisting of optionally substituted carbocycle or optionally substituted heterocycle; or alternatively, $R^{12}$ and $R^{13}$ or $R^9$ and $R^{10}$ can come together to form a spiro compound selected from the group consisting of optionally substituted or optionally substituted heterocycle.

A compound of the Formula (XIII) or (XIV):

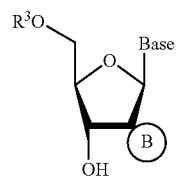
(XIII)

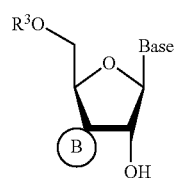
(XIV)

or a pharmaceutically acceptable salt thereof, wherein:

$R^3$ is selected from the group consisting of H; mono-, di-, and tri-phosphate or a stabilized phosphate prodrug; acyl; a sulfonate ester; optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein $R^3$ is independently H, or mono-, di- or triphosphate; B indicates a spiro compound selected from the group consisting of optionally substituted carbocycle or optionally substituted heterocycle;

Base is selected from the group consisting of:

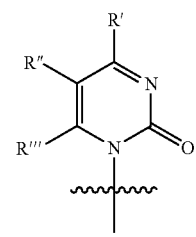
(a)

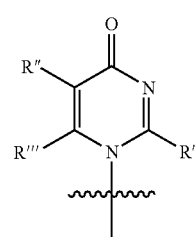
(b)

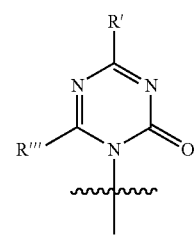
(c)

-continued

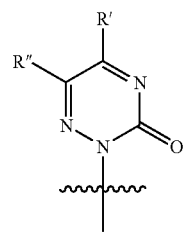
(d)

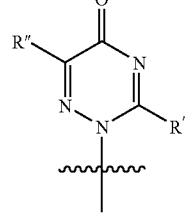
(e)

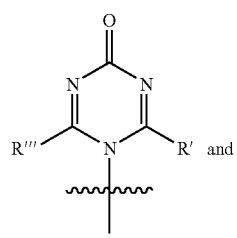
(f)

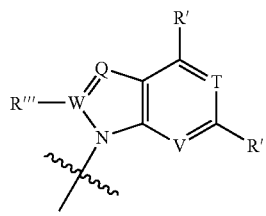
(g)

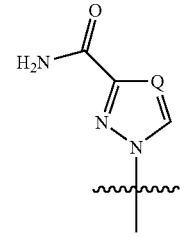
(h)

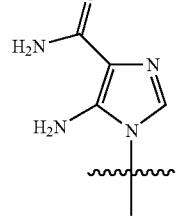
(i)

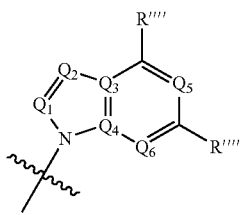
(j)

and wherein each R', R'', R''', and R'''' are independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_m$ OH, $(CH_2)_m NH_2$, $(CH_2)_m COOH$, $(CH_2)_m CN$, $(CH_2)_m NO_2$, and $(CH_2)_m CONH_2$;

m is 0 or 1;

W is C—R'' or N;

T and V independently are CH or N;

Q is CH, —CCl, —CBr, —CF, —CI, —CCN, —C—COOH, —C—$CONH_2$, or N;

$Q_1$, and $Q_2$ independently are N or C—R;

R is H, alkyl, or acyl; and $Q_3$, $Q_4$, $Q_5$ and $Q_6$ independently are N or CH.

A compound of Formula (XV), (XVI), (XVII), (XVIII) or (XIX):

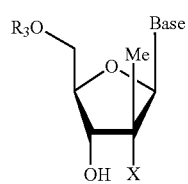

(XV)

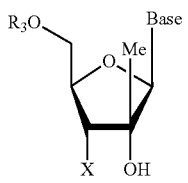

(XVI)

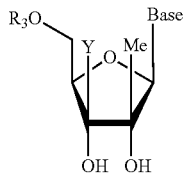

(XVII)

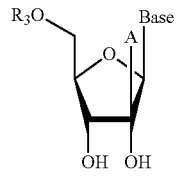

(XVIII)

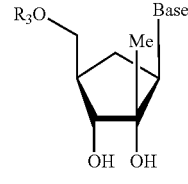

XIX or a pharmaceutically acceptable salt thereof, wherein:

A is selected from the group consisting of optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_m COOH$, $(CH_2)_m COOR$, $(CH_2)_m CONH_2$, $(CH_2)_m CONR_2$, and $(CH_2)_m CONHR$;

Y is selected from the group consisting of H, optionally substituted lower alkyl, cycloalkyl, alkenyl, alkynyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$, $CF_2CF_3$, $CH_2CO_2R$, $(CH_2)_m COOH$, $(CH_2)_m COOR$, $(CH_2)_m CONH_2$, $(CH_2)_m CONR_2$, and $(CH_2)_m CONHR$;

R is H, alkyl, or acyl;

X is selected from the group consisting of —OH, optionally substituted alkyl, cycloalkyl, alkenyl, alkynyl, —O-alkyl, —O-alkenyl, —O-alkynyl, —O-aryl, —O-aralkyl, —O-cycloalkyl, O-acyl, F, Cl, Br, I, CN, NC, SCN, OCN, NCO, $NO_2$, $NH_2$, $N_3$, NH-acyl, NH-alkyl, N-dialkyl, NH-alkenyl, NH-alkynyl, NH-aryl, NH-aralkyl, NH-cycloalkyl, SH, S-alkyl, S-alkenyl, S-alkynyl, S-aryl, S-aralkyl, S-acyl, S-cycloalkyl, $CO_2$-alkyl, CONH-alkyl, CON-dialkyl, CONH-alkenyl, CONH-alkynyl, CONH-aralkyl, CONH-cycloalkyl, $CH_2OH$, $CH_2NH_2$, $CH_2NHCH_3$, $CH_2N(CH_3)_2$, $CH_2F$, $CH_2Cl$, $CH_2N_3$, $CH_2CN$, $CH_2CF_3$, $CF_3$,$CF_2CF_3$, $CH_2CO_2R$, $(CH_2)_m COOH$, $(CH_2)_m COOR$, $(CH_2)_m CONH_2$, $(CH_2)_m CONR_2$, $(CH_2)_m CONHR$, an optionally substituted 3-7 membered carbocyclic, and an optionally substituted 3-7 membered heterocyclic ring having O, S, and/or N independently as a heteroatom taken alone or in combination;

m is 0 or 1;

$R^3$ is selected from the group consisting of H; mono-, di-, and tri-phosphate or a stabilized phosphate prodrug; substituted or unsubstituted alkyl; acyl; a sulfonate ester; optionally substituted alkyl sulfonyl; optionally substituted arylsulfonyl; a lipid; an amino acid; a carbohydrate; a peptide; cholesterol; and a pharmaceutically acceptable leaving group which when administered in vivo is capable of providing a compound wherein $R^3$ is independently H, or mono-, di- or triphosphate; and Base is a non-natural base selected from the group of:

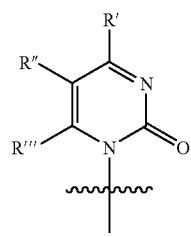

(a)

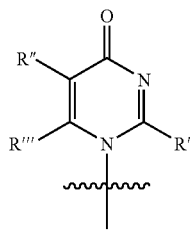

(b)

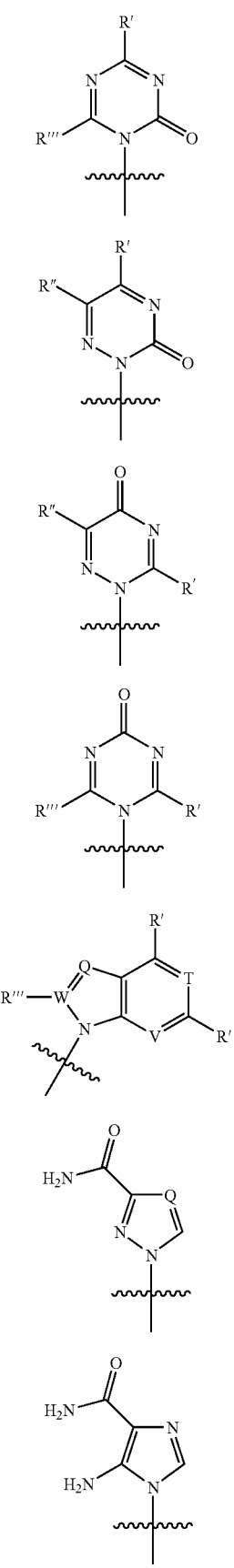

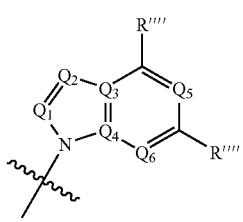

wherein: each R', R'', R''', and R'''' is independently selected from the group consisting of H, OH, substituted or unsubstituted alkyl, substituted or unsubstituted alkenyl, substituted or unsubstituted alkynyl, cycloalkyl, Br-vinyl, —O-alkyl, O-alkenyl, O-alkynyl, O-aryl, O-aralkyl, —O-acyl, O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, F, Cl, Br, I, CN, COOH, $CONH_2$, $CO_2$-alkyl, CONH-alkyl, CON-dialkyl, OH, $CF_3$, $CH_2OH$, $(CH_2)_m$ OH, $(CH_2)_m NH_2$, $(CH_2)_m COOH$, $(CH_2)_m CN$, $(CH_2)_m NO_2$, and $(CH_2)_m CONH_2$;

m is 0 or 1;

W is C—R'' or N;

T and V independently are CH or N;

Q is CH, —CCl, —CBr, —CF, —Cl, —CCN, —C—COOH, —C—$CONH_2$, or N;

$Q_1$ and $Q_2$ independently are N or C—R''''; and $Q_3$, $Q_4$, $Q_5$, and $Q_6$ independently are N or CH;

with the proviso that in bases (g) and (i), R', R'''' are not H, OH, or $NH_2$; and Q, T, V, $Q_2$, $Q_5$, and $Q_6$ are not N.

In a particular embodiment of the present invention, a compound of the Formula:

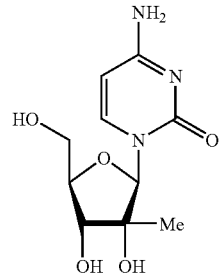

or its pharmaceutically acceptable salt or prodrug thereof, is provided for the treatment or prophylaxis of Norovirus or Saporovirus infection. This compound can be synthesized, for example, using the methods described in Harry-O'kuru, R. E.; Smith, J. M.; Wolfe, M. S. A short, flexible route toward 2'-C-branched ribonucleosides. J. Org. Chem. 1997, 62, 1754-1759.

Prodrugs and Derivatives

The active compound can be administered as any salt or prodrug that upon administration to the recipient is capable of providing directly or indirectly the parent compound, or that exhibits activity itself. Non-limiting examples are the pharmaceutically acceptable salts (alternatively referred to as "physiologically acceptable salts"), and a compound, which has been alkylated, acylated, or otherwise modified at the 5'-position, or on the purine or pyrimidine base (a type of "pharmaceutically acceptable prodrug").

Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

Pharmaceutically Acceptable Salts

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed by addition of acids, which form a physiological acceptable anion, for example, tosylate, methanesulfonate, acetate, citrate, malonate, tartrate, succinate, benzoate, ascorbate, a-ketoglutarate, a-glycerophosphate, formate, fumarate, propionate, glycolate, lactate, pyruvate, oxalate, maleate, and salicylate. Suitable inorganic salts may also be formed, including, sulfate, nitrate, bicarbonate, carbonate salts, hydrobromate and phosphoric acid. In a preferred embodiment, the salt is a mono- or di-hydrochloride salt.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made. In one embodiment, the salt is a hydrochloride salt of the compound. In another embodiment, the pharmaceutically acceptable salt is a dihydrochloride salt.

Nucleotide Prodrug Formulations

The nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono-, di- or triphosphate of the nucleoside reduces polarity and allows passage into cells. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischoferger, Antiviral Research, 1995, 27: 1-17. Any of these can be used in combination with the disclosed nucleosides to achieve a desired effect.

In an alternative embodiment, the nucleoside is delivered as a phosphonate or a SATE derivative.

The active nucleoside can also be provided as a 2', 3' and/or 5'-phosphoether lipid or a 2', 3' and/or 5'-ether lipid. Non-limiting examples are described include the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." AIDS Res. Hum. Retroviruses. 6: 491-501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." J. Med. Chem. 34: 1408.1414; Hosetller, K. Y., D. D. Richman, D. A. Carson, L. M. Stuhmiller, G. M. T. van Wijk, and H. van den Bosch. 1992. "Greatly enhanced inhibition of human immunodeficiency virus type I replication in CEM and HT4-6C cells by 3'-deoxythymine diphosphate dimyristoylglycerol, a lipid prodrug of 3',-deoxythymine. "Antimicrob. Agents Chemother. 36: 2025.2029; Hosetler, K.Y., L. M. Stuhmiller, H. B. Lenting, H. van den Bosch, and D. D. Richman, 1990. "Synthesis and antiretroviral activity of phospholipid analogs of azidothymine and other antiviral nucleosides." J. Biol. Chem. 265: 61127.

Nonlimiting examples of U.S. patents that disclose suitable lipophilic substituents that can be covalently incorporated into the nucleoside, preferably at the 2', 3' and/or 5'-OH position of the nucleoside or lipophilic preparations, include U.S. Pat. Nos. 5,149,794 (Sep. 22, 1992, Yatvin et al.); 5,194,654 (Mar. 16, 1993, Hostetler et al., 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

Aryl esters, especially phenyl esters, are also provided. Nonlimiting examples are disclosed in DeLambert et al., J. Med. Chem. 37: 498 (1994). Phenyl esters containing a carboxylic ester ortho to the phosphate are also provided. Khamnei and Torrence, J. Med. Chem.; 39: 4109-4115 (1996). In particular, benzyl esters, which generate the parent compound, in some cases using substituents at the ortho- or para-position to accelerate hydrolysis, are provided. Examples of this class of prodrugs are described by Mitchell et al., J. Chem. Soc. Perkin Trans. I 2345 (1992); Brook, et al. WO 91/19721; and Glazier et al. WO 91/19721.

Cyclic and noncyclic phosphonate esters are also provided. Nonlimiting examples are disclosed in Hunston et al., J. Med. Chem. 27: 440-444 (1984) and Starrett et al. J. Med. Chem. 37: 1857-1864 (1994). Additionally, cyclic 3',5'-phosphate esters are provided.

Nonlimiting examples are disclosed in Meier et al. J. Med. Chem. 22: 811-815 (1979).

Cyclic 1',3'-propanyl phosphonate and phosphate esters, such as ones containing a fused aryl ring, i.e. the cyclosaligenyl ester, are also provided (Meier et al., Bioorg. Med. Chem. Lett. 7: 99-104 (1997)). Unsubstituted cyclic 1',3'-propanyl esters of the monophosphates are also provided (Farquhar et al., J. Med. Chem. 26: 1153 (1983); Farquhar et al., J. Med. Chem. 28: 1358 (1985)) were prepared. In addition, cyclic 1',3'-propanyl esters substituted with a pivaloyloxy methyloxy group at C-1' are provided (Freed et al., Biochem. Pharmac. 38: 3193 (1989); Biller et al., U.S. Pat. No. 5,157,027).

Cyclic phosphoramidates are known to cleave in vivo by an oxidative mechanism.

Therefore, in one embodiment of the present invention, a variety of substituted 1', 3' propanyl cyclic phosphoramidates are provided. Non-limiting examples are disclosed by Zon, Progress in Med. Chem. 19, 1205 (1982). Additionally, a number of 2'- and 3'-substituted proesters are provided. 2'-Substituents include methyl, dimethyl, bromo, trifluoromethyl, chloro, hydroxy, and methoxy; 3'-substituents including phenyl, methyl, trifluoromethyl, ethyl, propyl, i-propyl, and cyclohexyl. A variety of 1'-substituted analogs are also provided.

Cyclic esters of phosphorus-containing compounds are also provided. Non-limiting examples are described in the following: [1] di and tri esters of phosphoric acids as reported in Nifantyev et al., Phosphorus, Sulfur, Silicon and Related Elements, 113: 1 (1996); Wijnberg et al., EP-180276 A1; * [2] phosphorus (III) acid esters. Kryuchkov et al., Izv. Akad. Nauk SSSR, Ser. Khim. 6: 1244 (1987). Some of the compounds were claimed to be useful for the asymmetric synthesis of L-Dopa precursors. Sylvain et al., DE3512781 A1; *[3] phosphoramidates. Shih et al., Bull. Inst. Chem. Acad. Sin, 41: 9 (1994); Edmundson et al., J. Chem. Res. Synop. 5: 122 (1989); and *[4] phosphonates. Neidlein et al., Heterocycles 35: 1185 (1993).

Further, nonlimiting examples of U.S. and International Patent Applications that disclose suitable cyclic phosphoramidate prodrugs include U.S. Pat. No. 6,312,662; WO 99/45016; WO 00/52015; WO 01/47935; and WO 01/18013 to Erion, et al. from Metabasis Therapeutics, Inc. Specifically, prodrugs of the formula below are provided:

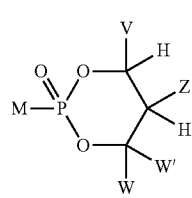

(A*)

wherein: together V and Z are connected via an additional 3-5 atoms to form a cyclic group containing 5-7 atoms, optionally 1 heteroatom, substituted with hydroxy, acyloxy, alkoxycarbonyloxy, or aryloxycarbonyloxy attached to a carbon atom that is three atoms from both O groups attached to the phosphorus; or together V and Z are connected via an additional 3-5 atoms to form a cyclic group, optionally containing 1 heteroatom, that is fused to an aryl group at the beta, and gamma position to the O attached to the phosphorus; together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from an O attached to the phosphorus; together Z and W are connected via an additional 3-5 atoms to form a cyclic group, optionally containing one heteroatom, and V must be aryl, substituted aryl, heteroaryl, or substituted heteroaryl; together W and W' are connected via an additional 2-5 atoms to form a cyclic group, optionally containing 0-2 heteroatoms, and V must be aryl, substituted aryl, heteroaryl, or substituted heteroaryl; Z is selected from the group consisting of —CHR$^2$OH, —CHR$^2$OC(O)R$^3$, —CHR$^2$OC(S)R$^3$, —CHR$^2$OC(S)OR$^3$, —CHR$^2$(O)SR$^3$, —CHR$^2$OCO$_2$R$^3$, —OR$^2$, —SR$^2$, —CHR$^2$N$_3$, —CH$_2$ aryl, —CH(aryl)OH, —CH(CH=CR$^2{}_2$)OH, —CH(C≡CR)OH, —R$^2$, —NR$^2{}_2$, —OCOR$^3$, —OCO$_2$R$^3$, —SCOR$^3$, —SCO$_2$R$^3$, —NHCOR$^2$, —NHCO$_2$R$^3$, —CR$_2$NHaryl, —(CR$_2$)$_p$—OR$^{12}$, and —(CR$_2$)$_p$—SR$^2$, p is an integer 2 or 3; with the provisos that: a) V, Z, W, W' are not all —H; and b) when Z is —R$^2$, then at least one of V, W, and W' is not —H, alkyl, aralkyl, or alicyclic;

R$^2$ is selected from the group consisting of R$^3$ and —H;

R$^3$ is selected from the group consisting of alkyl, aryl, alicyclic, and aralkyl;

R$^{12}$ is selected from the group consisting of —H, and lower acyl;

M is the biologically active agent, and that is attached to the phosphorus in Formula I via the 2', 3' and/or 5'-hydroxyl.

II. Compound Preparation

The nucleosides described herein can be synthesized by any means known in the art. In particular, the synthesis of the present nucleosides can be achieved by either alkylating the appropriately modified sugar followed by glycosylation, or glycosylation followed by alkylation of the nucleoside. The following non-limiting embodiments illustrate some general methodology to obtain the nucleosides of the present invention.

A. General Synthesis of 1'-C-Branched Nucleosides

1'-C-Branched ribonucleosides of the following structure:

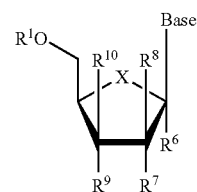

wherein Base, R$^1$, R$^2$, R$^3$, R$^4$, R$^5$, R$^6$, R$^7$, R$^8$, R$^9$, R$^{10}$, Y, W$^1$, W$^2$, W$^3$, X, X$^1$, X$^2$ and X$^3$ are as defined herein can be prepared by one of the following general methods.

Modification from the Lactone

The key starting material for this process is an appropriately substituted lactone.

The lactone can be purchased or can be prepared by any known means including standard epimerization, substitution and cyclization techniques. The lactone can be optionally protected with a suitable protecting group, preferably with an acyl or silyl group, by methods well known to those skilled in the art, as taught by Greene et al. Protective Groups in Organic Synthesis, John Wiley and Sons, Second Edition, 1991. The protected lactone can then be coupled with a suitable coupling agent, such as an organometallic carbon nucleophile, such as a Grignard reagent, an organolithium, lithium dialkylcopper or R$^6$—SiMe$_3$ in TBAF with the appropriate non-protic solvent at a suitable temperature to give the 1'-alkylated sugar.

The optionally activated sugar can then be coupled to the BASE by methods well known to those skilled in the art, as taught by Townsend Chemistry of Nucleosides and Nucleotides, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al. Protective Groups in Organic Synthesis, John Wiley and Sons, Second Edition, 1991.

In a particular embodiment, the 1'-C-branched ribonucleoside is desired. The synthesis of a ribonucleoside is shown in Scheme 1. Alternatively, deoxyribo-nucleoside is desired. To obtain these nucleosides, the formed ribonucleoside can optionally be protected by methods well known to those skilled in the art, as taught by Greene et al. Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

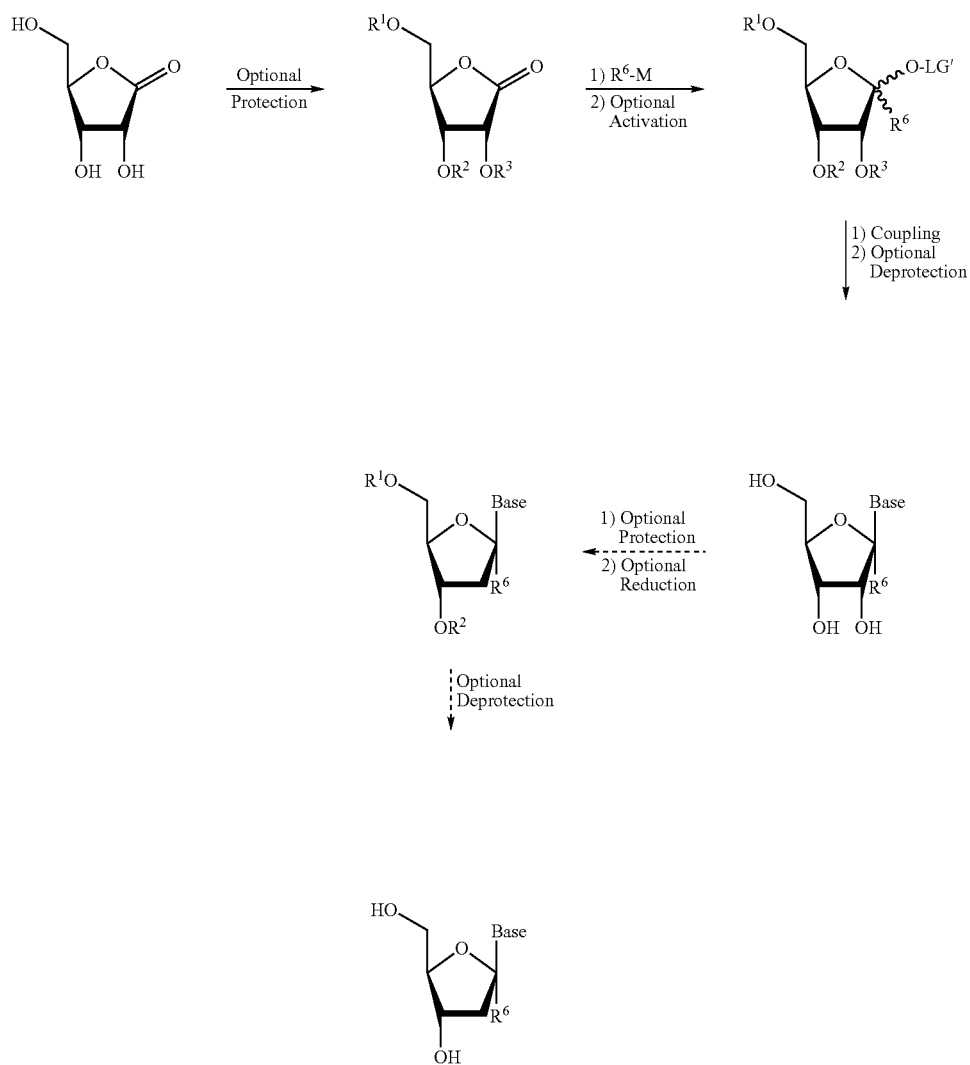

Scheme 1

Alternative Method for the Preparation of 1'-C-Branched Nucleosides

The key starting material for this process is an appropriately substituted hexose. The hexose can be purchased or can be prepared by any known means including standard epimerization (e.g. via alkaline treatment), substitution and coupling techniques. The hexose can be selectively protected to give the appropriate hexa-furanose, as taught by Townsend Chemistry of Nucleosides and Nucleotides, Plenum Press, 1994.

The 1'-hydroxyl can be optionally activated to a suitable leaving group such as an acyl group or a halogen via acylation or halogenation, respectively. The optionally activated sugar can then be coupled to the BASE by methods well known to those skilled in the art, as taught by Townsend Chemistry of Nucleosides and Nucleotides, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

The 1'-CH$_2$—OH, if protected, can be selectively deprotected by methods well known in the art. The resultant primary hydroxyl can be functionalized to yield various C-branched nucleosides. For example, the primary hydroxyl can be reduced to give the methyl, using a suitable reducing agent. Alternatively, the hydroxyl can be activated prior to reduction to facilitate the reaction; i.e. via the Barton reduction. In an alternate embodiment, the primary hydroxyl can be oxidized to the aldehyde, then coupled with a carbon nucleophile, such as a Grignard reagent, an organolithium, lithium dialkylcopper or R$^6$—SiMe$_3$ in TBAF with the appropriate non-protic solvent at a suitable temperature.

In a particular embodiment, the 1'-C-branched ribonucleoside is desired. The synthesis of a ribonucleoside is shown in Scheme 2. Alternatively, deoxyribo-nucleoside is desired. To obtain these nucleosides, the formed ribonucleoside can optionally be protected by methods well known to those skilled in the art, as taught by Greene et al. Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 2

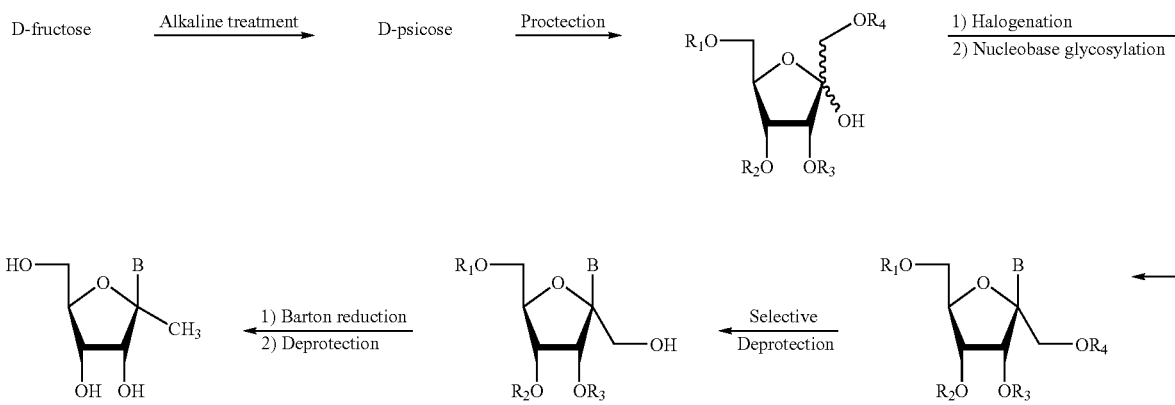

In addition, the L-enantiomers corresponding to the compounds of the invention can be prepared following the same general methods (1 or 2), beginning with the corresponding L-sugar or nucleoside L-enantiomer as starting material.

B. General Synthesis of 2'-C-Branched Nucleosides

2'-C-Branched ribonucleosides of the following structure:

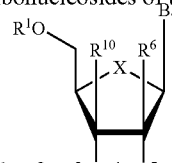

wherein Base, $R^1$, $R^2$, $R^3$, $R^4$, $R^5$, $R^6$, $R^7$, $R^9$, $R^{10}$, Y, $W^1$, $W^2$, $W^3$, X, $X^1$, $X^2$ and $X^3$ are as defined herein can be prepared by one of the following general methods.

Glycosylation of the Nucleobase with an Appropriately Modified Sugar

The key starting material for this process is an appropriately substituted sugar with a 2'-OH and 2'-H, with the appropriate leaving group (LG), for example an acyl group or a halogen. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr (VI) oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$—ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as taught by Greene et al. Protective Groups in Organic Synthesis, John Wiley and Sons, Second Edition, 1991.

The optionally protected sugar can then be coupled to the base by methods well known to those skilled in the art, as taught by Townsend Chemistry of Nucleosides and Nucleotides, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. Protective Groups in Organic Synthesis, John Wiley and Sons, Second Edition, 1991.

In a particular embodiment, the 2'-C-branched ribonucleoside is desired. The synthesis of a ribonucleoside is shown in Scheme 3. Alternatively, deoxyribo-nucleoside is desired. To obtain these nucleosides, the formed ribonucleoside can optionally be protected by methods well known to those skilled in the art, as taught by Greene et al. Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 3

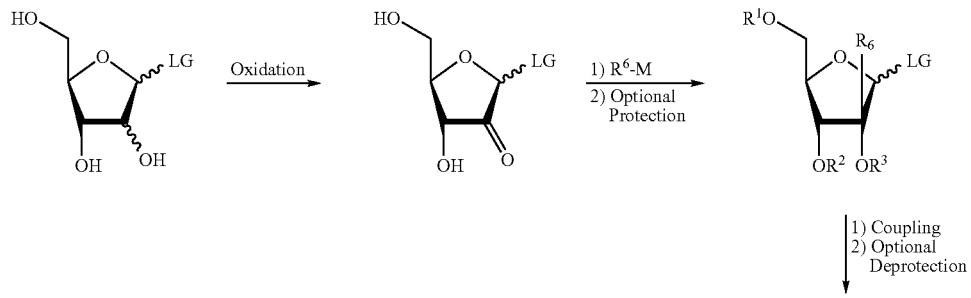

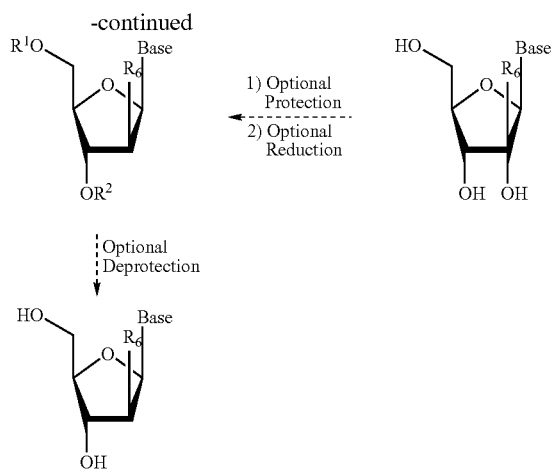

Modification of a Pre-Formed Nucleoside

The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. Protective Groups in Organic Synthesis, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxid with another ketone) and N bromosuccinimide.

Subsequently, the nucleoside can be deprotected by methods well-known to those skilled in the art, as taught by Greene et al. Protective Groups in Organic Synthesis, John Wiley and Sons, Second Edition, 1991.

In a particular embodiment, the 2'-C-branched ribonucleoside is desired. The synthesis of a ribonucleoside is shown in Scheme 4. Alternatively, deoxyribo-nucleoside is desired. To obtain these nucleosides, the formed ribonucleoside can optionally be protected by methods well known to those skilled in the art, as taught by Greene et al. Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 4

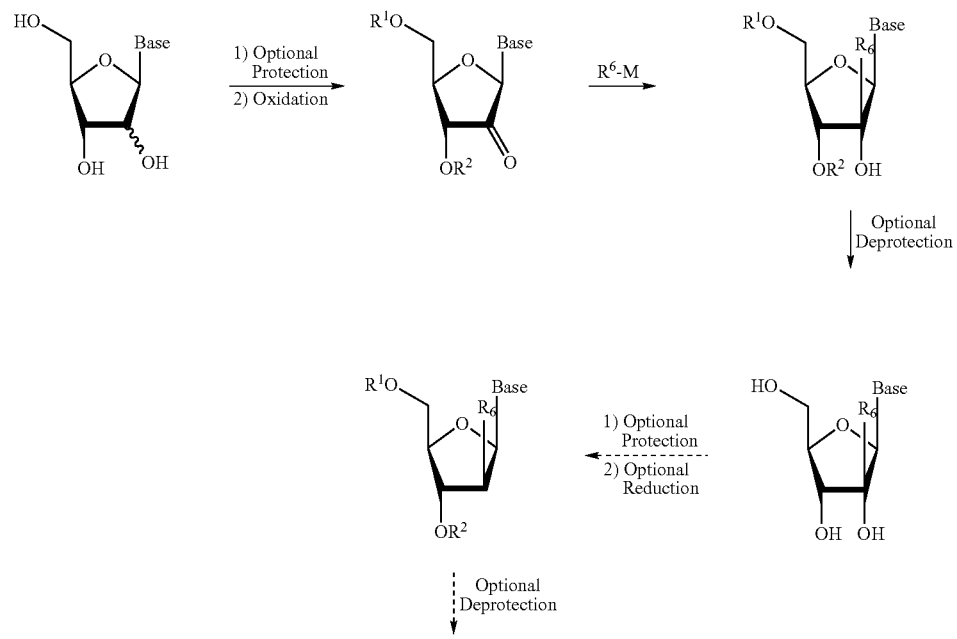

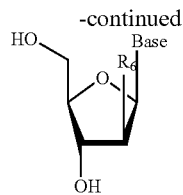

In another embodiment of the invention, the L-enantiomers are desired. Therefore, the L-enantiomers corresponding to the compounds of the invention can be prepared following the same foregoing general methods, beginning with the corresponding L-sugar or nucleoside L-enantiomer as starting material.

C. General Synthesis of 3'-C-Branched Nucleosides

3'-C-Branched ribonucleosides of the following structure:

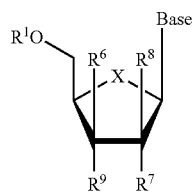

wherein Base, $R^1$, $R^2$, $R^3$, $R^4$, $R^5$, $R^6$, $R^7$, $R^8$, $R^9$, Y, $W^1$, $W^2$, $W^3$, X, $X^1$, $X^2$, and $X^3$ are as defined herein can be prepared by one of the following general methods.

I. Glycosylation of the Nucleobase with an Appropriately Modified Sugar

The key starting material for this process is an appropriately substituted sugar with a 3'-OH and 3'-H, with the appropriate leaving group (LG), for example an acyl group or a halogen. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 3'-modified sugar. Possible oxidizing agents are Jones reagent (a mixture of chromic acid and sulfuric acid), Collins's reagent (dipyridine Cr(VI) oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$—ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Then coupling of an organometallic carbon nucleophile, such as a Grignard reagent, an organolithium, lithium dialkylcopper or $R^6$—$SiMe_3$ in TBAF with the ketone with the appropriate non-protic solvent at a suitable temperature, yields the 3'-C-branched sugar.

The 3'-C-branched sugar can be optionally protected with a suitable protecting group, preferably with an acyl or silyl group, by methods well known to those skilled in the art, as taught by Greene et al. Protective Groups in Organic Synthesis. John Wiley and Sons, Second Edition, 1991.

The optionally protected sugar can then be coupled to the BASE by methods well known to those skilled in the art, as taught by Townsend Chemistry of Nucleosides and Nucleotides, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. Protective Groups in Organic Synthesis, John Wiley and Sons, Second Edition, 1991.

In a particular embodiment, the 3'-C-branched ribonucleoside is desired. The synthesis of a ribonucleoside is shown in Scheme 5. Alternatively, deoxyribo-nucleoside is desired. To obtain these nucleosides, the formed ribonucleoside can optionally be protected by methods well known to those skilled in the art, as taught by Greene et al. Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 5

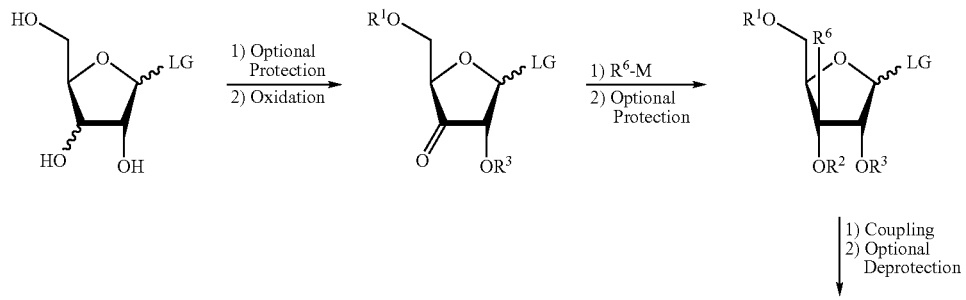

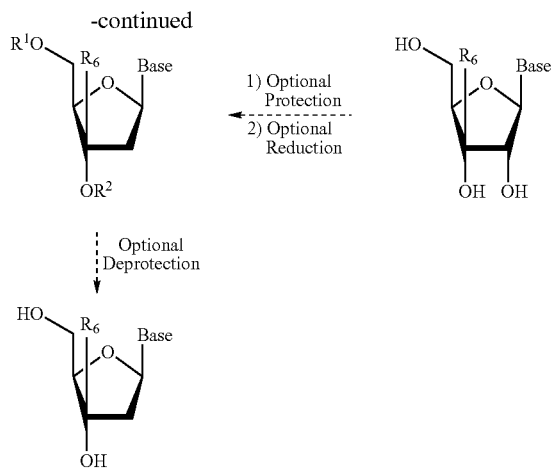

Modification of a Pre-Formed Nucleoside

The key starting material for this process is an appropriately substituted nucleoside with a 3'-OH and 3'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. Protective Groups in Organic Synthesis, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxid with another ketone) and N— bromosuccinimide.

Subsequently, the nucleoside can be deprotected by methods well known to those skilled in the art, as taught by Greene et al. Protective Groups in Organic Synthesis, John Wiley and Sons, Second Edition, 1991.

In a particular embodiment, the 3'-C-branched ribonucleoside is desired. The synthesis of a ribonucleoside is shown in Scheme 6. Alternatively, deoxyribo-nucleoside is desired. To obtain these nucleosides, the formed ribonucleoside can optionally be protected by methods well known to those skilled in the art, as taught by Greene et al. Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 6

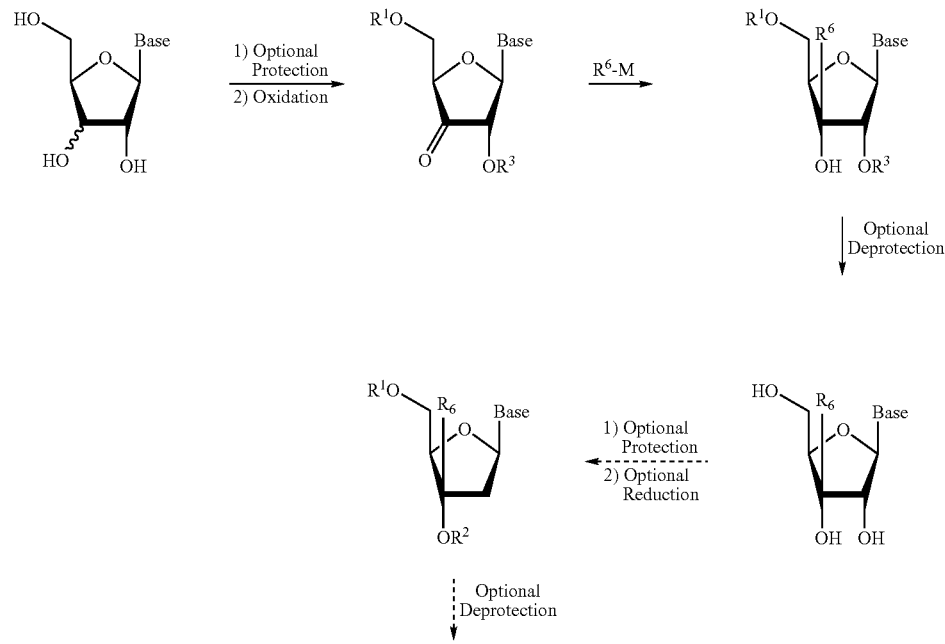

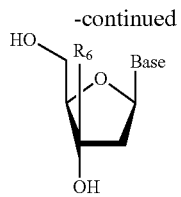

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

D. General Synthesis of 4'-C-Branched Nucleosides

4'-C-Branched ribonucleosides of the following structure:

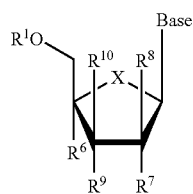

wherein Base, $R^1$, $R^2$, $R^3$, $R^4$, $R^5$, $R^6$, $R^7$, $R^8$, $R^9$, $R^{10}$, Y, $W^1$, $W^2$, $W^3$, X, $X^2$, $X^3$ and are as defined herein can be prepared by one of the following general methods.

Modification from the Pentodialdo-Furanose

The key starting material for this process is an appropriately substituted pentodialdo-furanose. The pentodialdo-furanose can be purchased or can be prepared by any known means including standard epimerization, substitution and cyclization techniques.

In a preferred embodiment, the pentodialdo-furanose is prepared from the appropriately substituted hexose. The hexose can be purchased or can be prepared by any known means including standard epimerization (e.g. via alkaline treatment), substitution and coupling techniques. The hexose can be either in the furanose form, or cyclized via any means known in the art, such as methodology taught by Townsend Chemistry of Nucleosides and Nucleotides, Plenum Press, 1994, preferably by selectively protecting the hexose, to give the appropriate hexafuranose.

The 4'-hydroxymethylene of the hexafuranose then can be oxidized with the appropriate oxidizing agent in a compatible solvent at a suitable temperature to yield the 4'-aldo-modified sugar. Possible oxidizing agents are Swern reagents, Jones reagent (a mixture of chromic acid and sulfuric acid), Collins's reagent (dipyridine Cr(VI) oxide), Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxid with another ketone) and N-bromosuccinimide, though preferably using $H_3PO_4$, DMSO, and DCC in a mixture of benzene/pyridine at room temperature.

Then, the pentodialdo-furanose can be optionally protected with a suitable protecting group, preferably with an acyl or silyl group, by methods well known to those skilled in the art, as taught by Greene et al. Protective Groups in Organic Synthesis. John Wiley and Sons, Second Edition, 1991. In the presence of a base, such as sodium hydroxide, the protected pentodialdo-furanose can then be coupled with a suitable electrophilic alkyl, halogeno-alkyl (i.e. $CF_3$), alkenyl or alkynyl (i.e. allyl), to obtain the 4'-alkylated sugar.

Alternatively, the protected pentodialdo-furanose can be coupled with the corresponding carbonyl, such as formaldehyde, in the presence of a base, such as sodium hydroxide, with the appropriate polar solvent, such as dioxane, at a suitable temperature, which can then be reduced with an appropriate reducing agent to give the 4'-alkylated sugar. In one embodiment, the reduction is carried out using PhOC(S)Cl, DMAP, preferably in acetonitrile at room temperature, followed by treatment of ACCN and TMSS refluxed in toluene.

The optionally activated sugar can then be coupled to the BASE by methods well known to those skilled in the art, as taught by Townsend Chemistry of Nucleosides and Nucleotides, Plenum Press, 1994. For example, an acylated sugar can be coupled to a silylated base with a Lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al., Protective Groups in Organic Synthesis, John Wiley and Sons, Second Edition, 1991.

In a particular embodiment, the 4'-C-branched ribonucleoside is desired.

Alternatively, deoxyribonucleoside is desired. To obtain these deoxyribo-nucleosides, a formed ribo-nucleoside can optionally be protected by methods well known to those skilled in the art, as taught by Greene et al., Protective Groups in Organic Synthesis, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In another embodiment of the invention, the L-enantiomers are desired. Therefore, the L-enantiomers corresponding to the compounds of the invention can be prepared following the same foregoing general methods, beginning with the corresponding L-pentodialdo-furanose as starting material.

E. General Synthesis of 2' and/or 3'-Prodrugs

The key starting material for this process is an appropriately substituted 1', 2', 3' or 4' branched β-D or β-L nucleoside. The branched nucleoside can be purchased or can be prepared by any known means including the techniques disclosed herein. The branched nucleoside can be optionally protected with a suitable protecting group, preferably with a silyl group, by methods well known to those skilled in the art, as taught by Greene et al. Protective Groups in Organic Synthesis, John Wiley and Sons, Second Edition, 1991. The protected branched nucleoside can then be coupled with a suitable acyl donor, such as an acyl chloride and/or an acyl anhydride with the appropriate protic or aprotic solvent at a suitable temperature, to give the 2' and/or 3'-prodrug of 1', 2', 3' or 4' branched β-D or β-L nucleoside. Alternatively, the protected branched nucleoside can then be coupled with a suitable acyl, such as a carboxylic acid, such as alkanoic acid and/or amino acid residue, optionally with a suitable coupling agent, with the appropriate aprotic solvent at a suitable temperature, to give the 2' and/or 3'-prodrug of 1', 2', 3' or 4' branched β-D or β-L nucleoside. Possible coupling reagents are any reagents that promote coupling, including but not limited to, Mitsunobu reagents (e.g. diisopropyl azodicarboxylate and diethyl azodicarboxylate) with triphenylphosphine or various carbodiimides.

For example, simple amino-alcohols can be esterified using acid chlorides in refluxing acetonitrile-benzene mixture (See Scheme 7 below: Synthetic Communications, 9 1978, 8 (5), 327-333; hereby incorporated by reference). Alternatively, esterification can be achieved using an anhydride, as described in J. Am. Chem. Soc., 1999, 121 (24), 5661-5664, which is hereby incorporated by reference. See FIGS. 2, 3, and 4.

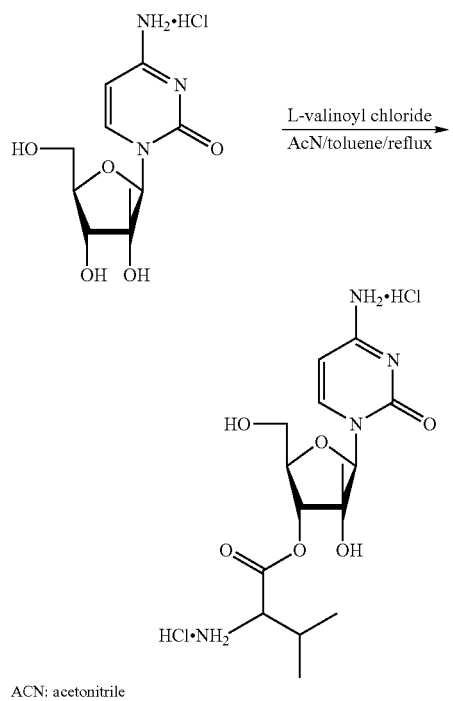

Scheme 7

ACN: acetonitrile

The synthesis of individual compounds described herein can be found, for example, in PCT WO 2004/002999, the contents of which are hereby incorporated by reference.

III. Pharmaceutical Compositions

A preferred dose of the compound for treatment or prophylaxis of an infection by a Norovirus will be in the range from about 1 to 50 mg/kg, preferably 1 to 20 mg/kg, of body weight per day, more generally 0.1 to about 100 mg per kilogram body weight of the recipient per day. Lower doses may be preferable, for example doses of 0.5-100 mg, 0.5-50 mg, 0.5-10 mg, or 0.5-5 mg per kilogram body weight per day. Even lower doses may be useful, and thus ranges can include from 0.1-0.5 mg per kilogram body weight per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in any unit suitable dosage form, including but not limited to one containing 7 to 3000 mg, preferably 70 to 1400 mg of active ingredient per unit dosage form. An oral dosage of 50-1000 mg is usually convenient, including in one or multiple dosage forms of 50, 100, 200, 250, 300, 400, 500, 600, 700, 800, 900, or 1000 mgs. Lower doses may be preferable, for example from 10-100 or 1-50 mg. Also contemplated are doses of 0.1-50 mg, or 0.1-20 mg or 0.1-10.0 mg.

Furthermore, lower doses may be utilized in the case of administration by a non-oral route, as, for example, by injection or inhalation.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. The parental preparation can be enclosed in ampoules, disposable syringes, or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will either apparent to those skilled in the art. The materials can also be obtained commercially from Alza Corporation (Mountain View, Calif.).

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachidoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Optional Additional Components

In addition to the antiviral compounds described herein, other compounds can also be present. For example, type I interferon (IFN) is known to inhibit Norovirus replication. Certain vitamins, particularly vitamin C, are believed to be effective at treating certain viral infections. One study has shown that Vitamin A supplementation reduced the prevalence of Norovirus GII infections, increased the length of both Norovirus GI and GII shedding, and decreased the prevalence of NoV-associated diarrhea (1: J Infect Dis. 2007 Oct. 1; 196(7):978-85. Epub 2007 Aug. 22). Lysine is known as an antiviral agent. It is also known that virus-like particles (VLPs) derived from genogroup II (GII) Norovirus were bound to cell surface heparan sulfate proteoglycan and other negatively charged glycosaminoglycans. To treat the symptoms of infection, one can also administer an anti-emetic, an anti-diarrheal agent, and/or an analgesic.

IV. Methods of Treatment

The compounds and pharmaceutical compositions described herein can be used to treat or prevent an infection by one or more Noroviruses, as well as other viruses in the Caliciviridae taxonomic family.

In therapeutic use for treating Norovirus infection, the compounds and/or compositions can be administered to patients diagnosed with Norovirus infection at dosage levels suitable to achieve therapeutic benefit. By "therapeutic benefit," and grammatical equivalents, is meant the administration of the compound leads to a beneficial effect in the patient over time. For example, therapeutic benefit can be achieved when the Norovirus titer or viral load in a patient is either reduced or stops increasing.

Therapeutic benefit also can be achieved if the administration of a compound slows or halts altogether the onset of adverse symptoms that typically accompany Norovirus infections, regardless of the Norovirus titer or viral load in the patient. The compounds and/or compositions described herein may also be administered prophylactically in patients who are at risk of developing Norovirus infection, or who have been exposed to Norovirus, to prevent the development of Norovirus infection. For example, the compounds and/or compositions thereof may be administered to patients likely to have been exposed to Norovirus.

Outbreaks of norovirus disease often occur in closed or semi-closed communities, such as long-term care facilities, hospitals, prisons, and cruise ships where once the virus has been introduced, the infection spreads very rapidly by either person-to-person transmission or through contaminated food. Many norovirus outbreaks have been traced to food that was handled by one infected person. Accordingly, it may be advantageous to provide prophylactic doses of the compounds described herein to individuals in these facilities who are likely to come into contact with Norovirus or other Caliciviridae.

V. High Throughput Screening Methods

Both Norovirus replicons and Hepatitis C replicons require viral helicase, protease, and polymerase to be functional in order for replication of the replicon to occur. Norovirus replicons can be used in high throughput assays, which evaluate whether a compound to be screened for activity inhibits the ability of Norovirus helicase, protease, and/or polymerase to function, as evidenced by an inhibition of replication of the replicon.

Replicon-based screening assays for antiviral therapy are known in the art. One such assay is described, for example, in Puig-Basagoiti et al., Antimicrobial Agents and Chemotherapy, December 2005, p. 4980-4988, Vol. 49, No. 12, the contents of which are hereby incorporated by reference.

Puig-Basagoiti developed high-throughput assays using a luciferase-expressing replicon, virus-like particles, and full-length virus, to discover drugs useful in treating West Nile Virus infection. Analogous high-throughput assays can be used, using Norovirus replicons, to evaluate compounds described herein, and other compounds and compound libraries, for the ability of compounds to treat or prevent Noroviral infection.

The development of Norovirus chemotherapy can benefit from reliable high-throughput screening (HTS) assays. Although genetic systems have been developed for many Noroviruses, their usage in antiviral HTS assays has not been well explored.

Representative assay methods can include one or more of the following:

(i) an assay that uses a cell line harboring a persistently replicating subgenomic replicon (containing a deletion of viral structural genes), (ii) an assay that uses packaged virus-like particles containing replicon RNA, and (iii) an assay that uses a full-length virus with or without a reporter gene.

For example, a *Renilla* luciferase gene or other such luciferase gene can be engineered into a replicon as described herein, or into the full-length viral genome, to monitor viral replication. Other genes that lead to detectable proteins can also be used in addition to, or in place of, luciferase.

Potential inhibitors can then be identified through suppression of luciferase signals upon compound incubation. The antiviral assays can be optimized in a 96-well format, or higher throughput formats to identify inhibitor(s) through high throughput screening of a compound library, for example, a library including a plurality of the compounds described herein.

In addition, because each assay described above encompasses multiple but discrete steps of the viral life cycle, combinations of these systems can be used to discriminate the mode of action of any inhibitor among viral entry (detected by assays ii and iii but not by assay i), replication (including viral translation and RNA synthesis; detected by assays i to iii), and virion assembly (detected by assay iii but not by assays i and ii).

The present invention is described by way of illustration, in the following examples. It will be understood by one of ordinary skill in the art that these examples are in no way limiting and that variations of detail can be made without departing from the spirit and scope of the present invention.

Biological Assays

A number of assays are available to determine the potency of test compounds against viruses. Several of these biological assays are described in the examples below.

Example 1

Anti-Norovirus Activity

Compounds can exhibit anti-norovirus activity by inhibiting norovirus polymerase and/or helicase, by inhibiting other enzymes needed in the replication cycle, or by other pathways.

There is currently no approved pharmaceutical treatment for Norovirus infection (http://www.cdc.gov/ncidod/dvrd/revb/gastro/norovirus-qa.htm), and this has probably at least in part been due to the lack of availability of a cell culture system. Recently, a replicon system has been developed for the original Norwalk G-I strain (Chang, K. O., et al. (2006) Virology 353:463-473)

Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads. The infectivity assay may be useful for screening entry inhibitors.

Example 2

Phosphorylation Assay of Nucleoside to Active Triphosphate

To determine the cellular metabolism of the compounds, HepG2 cells are obtained from the American Type Culture Collection (Rockville, Md.), and are grown in 225 cm$^2$ tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of 2.5×10$^6$ cells per well in a 6-well plate and exposed to 10 μM of [$^3$H] labeled active compound (500 dpm/pmol) for the specified time periods.

The cells are maintained at 37° C. under a 5% $CO_2$ atmosphere. At the selected time points, the cells are washed three times with ice-cold phosphate-buffered saline (PBS).

Intracellular active compound and its respective metabolites are extracted by incubating the cell pellet overnight at −20° C. with 60% methanol followed by extraction with an additional 20 pal of cold methanol for one hour in an ice bath. The extracts are then combined, dried under gentle filtered air flow and stored at −20° C. until HPLC analysis.

Example 3

Bioavailability Assay in Cynomolgus Monkeys

The following procedure can be used to determine whether the compounds are bioavailable. Within 1 week prior to the study initiation, a cynomolgus monkey can be surgically implanted with a chronic venous catheter and subcutaneous venous access port (VAP) to facilitate blood collection and can undergo a physical examination including hematology and serum chemistry evaluations and the body weight recording. Each monkey (six total) receives approximately 250 μCi of $^3$H activity with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18-0 hours pre-dose, 0-4, 4-8 and 8-12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration (Cmax), time when the maximum concentration is achieved (TmaX), area under the curve (AUC), half life of the dosage concentration (TV), clearance (CL), steady state volume and distribution (Vss) and bioavailability (F).

Bone Marrow Toxicity Assay Human bone marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl) guanine for normal human hematopoietic progenitor cells in vitro" Antimicrobial Agents and Chemotherapy 1987; 31: 452-454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells "Biochemical Pharmacology 1992; 44: 1921-1925. The culture assays for CFU-GM and BFU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Example 4

Mitochondria Toxicity Assay

HepG2 cells are cultured in 12-well plates as described above and exposed to various concentrations of drugs as taught by Pan-Zhou X-R, Cui L, Zhou X-J, Sommadossi J-P, Darley-Usmer V M. "Differential effects of antiretroviral nucleoside analogs on mitochondrial function in HepG2 cells," Antimicrob. Agents Chemother. 2000; 44: 496-503.

Lactic acid levels in the culture medium after 4 day drug exposure are measured using a Boehringer lactic acid assay kit. Lactic acid levels are normalized by cell number as measured by hemocytometer count.

Example 5

Cytotoxicity Assay

Cells are seeded at a rate of between $5 \times 10^3$ and $5 \times 10^4$/well into 96-well plates in growth medium overnight at 37° C. in a humidified $CO_2$ (5%) atmosphere. New growth medium containing serial dilutions of the drugs is then added. After incubation for 4 days, cultures are fixed in 50% TCA and stained with sulforhodamine B. The optical density was read at 550 nm. The cytotoxic concentration was expressed as the concentration required to reduce the cell number by 50% ($EC_{50}$).

Example 6

Cell Protection Assay (CPA)

The assay is performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound," PNAS USA 2000, 97 (14), 7981-7986. MDBK cells (ATCC) are seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds are added to both infected and uninfected cells in a final concentration of 0.5% DMSO in growth medium. Each dilution is tested in quadruplicate. Cell densities and virus inocula are adjusted to ensure continuous cell growth throughout the experiment and to achieve more than 90% virus-induced cell destruction in the untreated controls after four days post-infection. After four days, plates are fixed with 50% TCA and stained with sulforhodamine B. The optical density of the wells is read in a microplate reader at 550 nm.

The 50% effective concentration ($EC_{50}$) values are defined as the compound concentration that achieved 50% reduction of cytopathic effect of the virus.

Example 7

Plaque Reduction Assay

For each compound the effective concentration is determined in duplicate 24-well plates by plaque reduction assays. Cell monolayers are infected with 100 PFU/well of virus. Then, serial dilutions of test compounds in MEM supplemented with 2% inactivated serum and 0.75% of methyl cellulose are added to the monolayers. Cultures are further incubated at 37° C. for 3 days, then fixed with 50% ethanol and 0.8% Crystal Violet, washed and air-dried. Then plaques are counted to determine the concentration to obtain 90% virus suppression.

Example 8

Yield Reduction Assay

For each compound the concentration to obtain a 6-log reduction in viral load is determined in duplicate 24-well plates by yield reduction assays. The assay is performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97 (14), 7981-7986, with minor modifications.

Briefly, MDBK cells are seeded onto 24-well plates ($2 \times 10^5$ cells per well) 24 hours before infection with BVDV (NADL strain) at a multiplicity of infection (MOI) of 0.1 PFU per cell. Serial dilutions of test compounds are added to cells in a final concentration of 0.5% DMSO in growth medium. Each dilution is tested in triplicate. After three days, cell cultures (cell monolayers and supernatants) are lysed by three freeze-thaw cycles, and virus yield is quantified by plaque assay. Briefly, MDBK cells are seeded onto 6-well plates ($5 \times 10^5$ cells per well) 24 h before use. Cells are inoculated with 0.2 mL of test lysates for 1 hour, washed and overlaid with 0.5% agarose in growth medium. After 3 days, cell monolayers are fixed with 3.5% formaldehyde and stained with 1% crystal violet (w/v in 50% ethanol) to visualize plaques. The plaques are counted to determine the concentration to obtain a 6-log reduction in viral load.

Example 9

Diagnosis of Norovirus Infection

One can diagnose a norovirus infection by detecting viral RNA in the stools of affected persons, using reverse transcription-polymerase chain reaction (RT-PCR) assays. The virus can be identified from stool specimens taken within 48 to 72 hours after onset of symptoms, although one can obtain satisfactory results using RT-PCR on samples taken as long as 7 days after the onset of symptoms. Other diagnostic methods include electron microscopy and serologic assays for a rise in titer in paired sera collected at least three weeks apart. There are also commercial enzyme-linked immunoassays available, but these tend to have relatively low sensitivity, limiting their use to diagnosis of the etiology of outbreaks. Clinical diagnosis of norovirus infection is often used, particularly when other causative agents of gastroenteritis have been ruled out.

Example 10

In Vitro Anti-Viral Activity

In vitro anti-viral activity can be evaluated in the following cell lines:

The Norwalk GI.1 strain (Chang, K. O., et al. (2006) Virology 353:463-473), the GII-4 strain replicon, as well other Norovirus replicons can be used in assays to determine the in vitro antiviral activity of the compounds described herein, or other compounds or compound libraries. In some embodiments, the replicon systems are subgenomic and therefore allow evaluation of small molecule inhibitors of non-structural proteins. This can provide the same benefits to Norovirus drug discovery that Hepatitis C replicons contributed to the discovery of therapeutics useful for treatment of that virus (Stuyver, L. J., et al. (2006) Antimicrob. Agents Chemother. 47:244-254). In fact, when the Norwalk GI.1 replicon was used in an assay as described by the preceeding reference, 2'-C-methyl-cytosine was determined to have an $EC_{50}$=2.1 µM and an $EC_{90}$=8.9 µM.

Both Norovirus replicons and Hepatitis C replicons require viral helicase, protease, and polymerase to be functional in order for replication of the replicon to occur. It is believed that the compounds described herein inhibit viral polymerase and/or viral helicase.

The in vitro cell culture infectivity assay reported using Norovirus genogroup I and II inoculums (Straub, T. M. et al. (2007) Emerg. Infect. Dis. 13(3):396-403) can also be used. This assay can be performed in a rotating-wall bioreactor utilizing small intestinal epithelial cells on microcarrier beads. The infectivity assay can be used for screening compounds for their ability to inhibit the desired virus.

Each of the publications referred to herein is hereby incorporated by reference in its entirety, for all purposes.

This invention has been described with reference to its preferred embodiments. Variations and modifications of the invention, will be obvious to those skilled in the art from the foregoing detailed description of the invention.

The invention claimed is:

1. A method for treating infections caused by a Caliciviridae virus, comprising administering an effective treatment amount of a compound of the formula

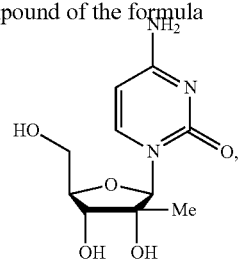

acyl and phosphate ester prodrugs thereof, or pharmaceutically-acceptable salts thereof.

2. The method of claim 1, wherein the virus is Norovirus or Saporovirus.

3. The method of claim 1, wherein the compound or pharmaceutically acceptable salt thereof is administered in combination or alternation with a second active agent.

4. The method of claim 3, wherein the second active agent is selected from the group consisting of an interferon, a negatively charged glycosaminoglycan, a vitamin, lysine, an anti-emetic, an anti-diarrheal agent, and an analgesic.

5. The method of claim 4, wherein the interferon is type I interferon (IFN).

6. The method of claim 4, wherein the second antiviral agent is a negatively charged glycosaminoglycan.

7. The method of claim 1, wherein the compound or pharmaceutically acceptable salt thereof is in the form of a dosage unit.

8. The method of claim 7, wherein the dosage unit contains 10 to 1500 mg of the compound and blood levels of 1-20 µM are achieved.

9. The method of claim 7, wherein the dosage unit is a tablet or capsule.

10. The method of claim 1, wherein the compound or pharmaceutically acceptable salt thereof is in substantially pure form.

11. The method of claim 1, wherein the compound or pharmaceutically acceptable salt thereof is at least 90% by weight of the β-D-isomer or the β-L-isomer.

12. The method of claim 1, wherein the compound or pharmaceutically acceptable salt thereof is at least 95% by weight of the β-D-isomer or the β-L-isomer.

13. The method of claim 1, wherein the compound is in the form of a pharmaceutically acceptable salt selected from the group consisting of a tosylate, methanesulfonate, acetate, citrate, malonate, tartrate, succinate, benzoate, ascorbate, α-ketoglutarate, α-glycerophosphate, formate, fumarate, propionate, glycolate, lactate, pyruvate, oxalate, maleate, salicylate, sulfate, nitrate, bicarbonate, carbonate salts, hydrobromate, hydrochloride, di-hydrochloride, and phosphoric acid salt.

14. The method of claim 13, wherein the pharmaceutically acceptable salt is a hydrochloride salt.

15. The method of claim 1, wherein the composition is administered topically, parenterally, or mucosally.

16. The method of claim 15, wherein the mucosal administration is intranasal, oral, intrarectal, or intravaginal.

17. The method of claim 1, wherein the compound is administered parenterally.

18. The method of claim 17, wherein the parenteral administration is transcutaneous.

19. A method for treating a Caliciviridae infection, comprising administering an effective treatment amount of a compound of the formula:

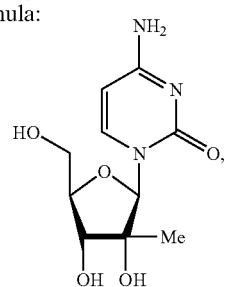

acyl or phosphate ester prodrugs thereof, or a pharmaceutically-acceptable salt thereof to a patient exposed to, anticipated to be exposed to, or infected by, a Caliciviridae virus.

20. The method of claim 19, wherein the virus is selected from the group consisting of Norovirus or Saporovirus.

21. The method of claim 19, wherein the treatment method involves the co-administration of a compound of the formula:

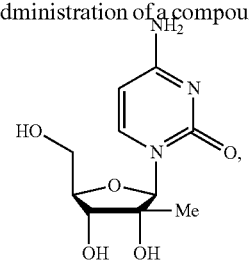

a prodrug thereof, or a pharmaceutically-acceptable salt thereof, in combination and/or alternation with one or more additional therapeutic agents selected from the group consisting of an interferon, a negatively charged glycosaminoglycan, a vitamin, lysine, an anti-emetic, an anti-diarrheal agent, and an analgesic.

* * * * *